United States Patent
Yang et al.

(10) Patent No.: US 10,976,388 B2
(45) Date of Patent: Apr. 13, 2021

(54) MINIMIZING INTRAVASCULAR MAGNETIC RESONANCE IMAGING (MRI) GUIDEWIRE HEATING WITH SINGLE LAYER MRI TRANSMIT/RECEIVE RADIO FREQUENCY COIL

(71) Applicant: Quality Electrodynamics, LLC, Mayfield Village, OH (US)

(72) Inventors: Xiaoyu Yang, Indiana, PA (US); Tsinghua Zheng, Chesterland, OH (US); Haoqin Zhu, Mayfield Village, OH (US)

(73) Assignee: Quality Electrodynamics, LLC, Mayfield Village, OH (US)

( * ) Notice: Subject to any disclaimer, the term of this patent is extended or adjusted under 35 U.S.C. 154(b) by 460 days.

(21) Appl. No.: 15/923,437

(22) Filed: Mar. 16, 2018

(65) Prior Publication Data

US 2018/0275226 A1    Sep. 27, 2018

Related U.S. Application Data

(60) Provisional application No. 62/476,288, filed on Mar. 24, 2017.

(51) Int. Cl.
*G01V 3/00* (2006.01)
*G01R 33/28* (2006.01)
(Continued)

(52) U.S. Cl.
CPC .......... *G01R 33/288* (2013.01); *A61B 5/055* (2013.01); *A61B 5/06* (2013.01); *A61M 25/0127* (2013.01);
(Continued)

(58) Field of Classification Search
CPC .............. G01R 33/543; G01R 33/5612; G01R 33/3607; G01R 33/5659; G01R 33/583
(Continued)

(56) References Cited

U.S. PATENT DOCUMENTS

| 4,680,549 A | 7/1987 | Tanttu |
| 4,825,162 A | 4/1989 | Roemer et al. |

(Continued)

FOREIGN PATENT DOCUMENTS

WO    20150043612 A1    4/2015

OTHER PUBLICATIONS

Notice of Allowance dated Jan. 10, 2020 in connection with U.S. Appl. No. 15/964,390.
(Continued)

*Primary Examiner* — Walter L Lindsay, Jr.
*Assistant Examiner* — Frederick Wenderoth
(74) *Attorney, Agent, or Firm* — Eschweiler & Potashnik, LLC

(57) ABSTRACT

A method for controlling an interventional magnetic resonance imaging (iMRI) system configured to control a heating mode of an iMRI guidewire, the method comprising: controlling, during an iMRI procedure, a magnitude of an induced current in a single-layer MRI radio frequency (RF) coil used in the iMRI procedure, or a phase of the induced current by adjusting at least one of: a difference between a working frequency of a whole body coil (WBC) used in the iMRI procedure and a resonant frequency of the single layer MRI RF coil, a coil loss resistance of the single layer MRI RF coil, or a blocking impedance of an LC circuit connected in parallel with the single-layer MRI RF coil; and controlling a heating mode of the guidewire based, at least in part on the magnitude or phase.

22 Claims, 23 Drawing Sheets

(51) Int. Cl.

| | |
|---|---|
| *A61M 25/09* | (2006.01) |
| *A61B 5/055* | (2006.01) |
| *A61M 25/01* | (2006.01) |
| *G01R 33/48* | (2006.01) |
| *G01R 33/36* | (2006.01) |
| *A61B 5/06* | (2006.01) |
| *G01R 33/34* | (2006.01) |
| *G01R 33/3415* | (2006.01) |

(52) U.S. Cl.
CPC ............ *A61M 25/09* (2013.01); *G01R 33/285* (2013.01); *G01R 33/3628* (2013.01); *G01R 33/48* (2013.01); *G01R 33/3415* (2013.01); *G01R 33/34046* (2013.01)

(58) Field of Classification Search
USPC ........................................................ 324/318
See application file for complete search history.

(56) References Cited

U.S. PATENT DOCUMENTS

| | | | |
|---|---|---|---|
| 4,987,370 A | 1/1991 | Leussler et al. | |
| 5,355,087 A | 10/1994 | Claiborne | |
| 5,386,191 A | 1/1995 | McCarten | |
| 5,455,595 A * | 10/1995 | Yokoyama | H01C 21/10 343/702 |
| 5,777,474 A * | 7/1998 | Srinivasan | G01R 33/34046 324/318 |
| 5,903,150 A | 5/1999 | Roznitsky | |
| 5,910,728 A | 6/1999 | Sodickson | |
| 6,177,797 B1 * | 1/2001 | Srinivasan | G01R 33/34046 324/318 |
| 6,249,121 B1 | 6/2001 | Boskamp | |
| 6,323,648 B1 | 11/2001 | Belt | |
| 6,529,005 B1 | 3/2003 | Kasten | |
| 6,791,328 B1 | 9/2004 | Nabetani | |
| 6,799,067 B2 | 9/2004 | Pacetti et al. | |
| 6,982,554 B2 | 1/2006 | Kurpad et al. | |
| 7,180,296 B2 | 2/2007 | Gross | |
| 7,663,367 B2 | 2/2010 | Wiggins | |
| 8,643,372 B2 | 2/2014 | Weiss | |
| 9,097,769 B2 | 8/2015 | Schillak | |
| 9,274,189 B2 | 1/2016 | Soutome | |
| 9,459,331 B2 | 10/2016 | Otake | |
| 9,541,614 B2 | 1/2017 | Soutome | |
| 9,638,771 B2 | 5/2017 | Soutome | |
| 9,880,242 B2 | 1/2018 | Darnell | |
| 10,168,402 B2 | 1/2019 | Gunamony | |
| 10,261,145 B2 | 4/2019 | Wald | |
| 10,324,147 B2 | 6/2019 | McNulty | |
| 2002/0169374 A1 | 11/2002 | Jevtic | |
| 2003/0097064 A1 | 5/2003 | Talpade et al. | |
| 2006/0071661 A1 | 4/2006 | Ong | |
| 2009/0121482 A1 * | 5/2009 | Rickard | F03B 15/00 290/44 |
| 2010/0022868 A1 | 1/2010 | Kocaturk | |
| 2010/0213941 A1 | 8/2010 | Driesel et al. | |
| 2011/0118723 A1 * | 5/2011 | Turner | A61B 18/1815 606/33 |
| 2012/0223709 A1 | 9/2012 | Schillak et al. | |
| 2012/0262173 A1 | 10/2012 | Soutome et al. | |
| 2012/0326515 A1 * | 12/2012 | Murai | H02J 50/12 307/72 |
| 2013/0063147 A1 * | 3/2013 | Findeklee | G01R 33/365 324/309 |
| 2013/0119991 A1 | 5/2013 | Soutome et al. | |
| 2013/0314091 A1 | 11/2013 | Otake et al. | |
| 2015/0260821 A1 | 9/2015 | Biber | |
| 2015/0323628 A1 | 11/2015 | Wald et al. | |
| 2015/0338478 A1 | 11/2015 | Schillak et al. | |
| 2016/0116556 A1 * | 4/2016 | Darnell | G01R 33/3875 324/307 |
| 2016/0209481 A1 | 7/2016 | Gunamony et al. | |
| 2016/0231400 A1 | 8/2016 | Fath et al. | |
| 2016/0254705 A1 * | 9/2016 | Jung | H02J 50/10 307/104 |
| 2016/0334479 A1 | 11/2016 | Poole et al. | |
| 2017/0146622 A1 | 5/2017 | Yang et al. | |
| 2018/0081008 A1 | 3/2018 | Yang | |
| 2018/0275233 A1 | 9/2018 | Yang | |
| 2018/0275234 A1 | 9/2018 | Han et al. | |
| 2018/0313918 A1 | 11/2018 | Yang | |
| 2018/0321339 A1 | 11/2018 | Yang | |
| 2018/0364318 A1 | 12/2018 | Yang | |
| 2020/0065020 A1 | 2/2020 | Tai | |

OTHER PUBLICATIONS

Non-Final Office Action dated Nov. 8, 2018 in connection with U.S. Appl. No. 15/583,345.
Notice of Allowance dated Apr. 10, 2019 in connection with U.S. Appl. No. 15/583,345.
Non-Final Office Action dated Nov. 18, 2019 in connection with U.S. Appl. No. 15/706,005.
W. Wang, et al., "Inductive Coupled Local TX Coil Design", Proc. Intl. Soc. Mag. Reson. Med. 18 (2010).
International Search Report and Written Opinion dated Nov. 9, 2017 in connection with International Patent Application No. PCT/US2017/042590.
U.S. Appl. No. 15/706,005, filed Sep. 15, 2017.
U.S. Appl. No. 15/583,345, filed May 1, 2017.
U.S. Appl. No. 15/933,860, filed Mar. 23, 2018.
U.S. Appl. No. 15/964,390, filed Apr. 27, 2018.
U.S. Appl. No. 15/971,075, filed May 4, 2018.
M. Etezadi-Amoli et al, "Controlling induced currents in guidewires using parallel transmit", Proc. Intl. Soc. Mag. Reson. Med. 18 (2010).
Konings et al., "Heating Around Intravascular Guidewires by Resonating RF Waves", JMRI 12 :79-85, 2000.
Natalia Gudino et al, "Parallel transmit excitation at 1.5 T based on the minimization of a driving function for device heating", Proc. Intl. Soc. Mag. Reson. Med. 21 (2013).
M. Etezadi-Amoli et al, "Transmit array concepts for improved MRI safety in the presence of long conductors", Proc. Intl. Soc. Mag. Reson. Med. 17 (2009).
Notice of Allowance dated Jul. 31, 2020 in connection with U.S. Appl. No. 15/706,005.
Wang J., "A Novel Method to Reduce the Signal Coupling of Surface Coils for MRI", Proc. ISMRM 4:1434 (1996).
Jovan Jevtic, "Ladder Networks for Capacitive Decoupling in Phased-Array Coils", Proc. Intl. Soc. Mag. Reson. Med 9 (2001).
Klaas P. Pruessmann et al, "SENSE: Sensitivity Encoding for Fast MRI", Magnetic Resonance in Medicine 42:952-962 (1999).
Ulrich Katscher et al, "Transmit Sense", Magnetic Resonance in Medicine 49:144-150 (2003).
U.S. Appl. No. 16/009,546, filed Jun. 15, 2018.

* cited by examiner

MINIMIZING INTRAVASCULAR MAGNETIC RESONANCE IMAGING (MRI) GUIDEWIRE HEATING WITH SINGLE LAYER MRI TRANSMIT/RECEIVE RADIO FREQUENCY COIL

RELATED APPLICATIONS

This application claims priority to and the benefit of U.S. Provisional Patent Application 62/476,288, filed Mar. 24, 2017.

BACKGROUND

Conventional approaches to interventional magnetic resonance imaging (iMRI) may result in unwanted radio frequency (RF) heating of endovascular (i.e., intravascular) guidewires or other metal devices used during an iMRI procedure. In a conventional iMRI procedure, a guidewire tip can reach a temperature of up to 74° C. after only thirty seconds of scanning. This level of heating is not safe for patients, limits the amount of imaging data that may be acquired, and thus minimizes the utility of endovascular guidewires used in iMRI. A typical iMRI procedure employs a whole body coil (WBC) as part of an MRI system. A WBC coil is a powerful RF transmitter that may generate more than 25 uT at 1.5 T and consume many KW of power. The guidewire may resonate with the WBC of the MRI system, causing excessive heating of the guidewire.

Conventional approaches to minimizing guidewire heating during iMRI procedures may use different types of guidewire. One approach uses a non-conductive core and non-magnetic wire. A second approach uses a transformer style guidewire in which a longer metal wire is broken into many small sections of metal wire. A third approach uses several layers of conductors and dielectric material. An issue that reduces the effectiveness of all three conventional approaches to mitigating unwanted RF heating is that a new kind of guidewire needs to be developed for each of the three different approaches, which renders the current metal wires available in the market unusable, thereby increasing costs.

Another approach to mitigating unwanted RF heating of guidewires during iMRI is to use parallel transmitting (pTx) coils as transmitting coils. A pTx approach includes many transmit (Tx) modes supported by pTx coils. By controlling the magnitude and phase of each transmit coil, the pTx coils can generate modes that induce little heat on a guidewire tip. A mode in this approach is defined as one combination of all transmitting coils in which each coil has its own unique magnitude and phase. In a pTx approach, a mode having lower induced heat compared to a conventional WBC approach may be defined as a low heat mode. There may be many low heat modes for pTx coils. The low heat modes are not as effective as a conventional WBC Tx field regarding Tx field uniformity but can still generate acceptable MRI images for iMRI applications. Examples of a parallel transmitting approach include M. Etezadi-Amoli et al, "Controlling induced currents in guidewires using parallel transmit", Proc. Intl. Soc. Mag. Reson. Med. 18 (2010), M. Etezadi-Amoli et al, "Transmit array concepts for improved MRI safety in the presence of long conductors", Proc. Intl. Soc. Mag. Reson. Med. 17 (2009), and Natalia Gudino et al, "Parallel transmit excitation at 1.5 T based on the minimization of a driving function for device heating", Proc. Intl. Soc. Mag. Reson. Med. 21 (2013). However, a drawback of the parallel transmitting approach is that it requires a dedicated pTx MRI system. Dedicated pTx MRI systems at 1.5 T and 3 T are not in wide use, and are extremely expensive. Furthermore, institutions may not wish to have duplicative MRI and pTx iMRI systems. This limits the usefulness of conventional pTx approaches for mitigating unwanted RF guidewire heating.

A magnetic resonance imaging (MRI) system, including an iMRI system, may include two kinds of MRI RF coils. The first kind of MRI RF coil is a transmit (Tx) coil. A Tx coil, while operating in Tx mode, transmits high power RF energy into the anatomy of the subject being imaged to excite nuclei spins in the tissue being imaged. The second kind of MRI RF coil is a receive (Rx) coil. An Rx coil, while operating in Rx mode, detects weak signals from nuclei spins of the anatomy being imaged. A conventional MRI system uses a built-in whole body coil (WBC) as a Tx coil. In a conventional MRI system, due to the geometric size of the WBC, the WBC applies RF energy to a much larger region of tissue than is required to image a given region of interest. For example, when a head scan is performed and a WBC is used, not only the head, but also the shoulders and chest also receive a high level of RF energy. This creates a high level specific absorption rate (SAR) issue which limits the clinical utility of MRI systems that use a conventional WBC/Rx coil approach. As a result, a local Tx coil is frequently used to mitigate the SAR problem.

A local Tx coil is designed to apply RF energy into only the anatomy being imaged. There are two conventional approaches to transmitting energy from a power source to a local Tx coil. A first conventional approach is to use a direct connection between the power source to the Tx coil using wires. A direct connection using wires is energy efficient because the energy loss in the connection wires is trivial. A disadvantage of direct connection using wires is that dedicated wiring is required, which increases the cost and complexity of the coil.

A second conventional approach to transmitting energy from a power source to a local Tx coil is to use inductive coupling. For the inductive coupling approach, a primary coil is directly connected to a power source. The primary coil may be a WBC or another large coil. The primary coil is a resonant LC circuit. A smaller second coil (i.e., a local coil) is also used. The second coil is another resonant circuit and is inductively coupled to the primary coil. Thus, energy can be transferred from the primary coil to the second coil. The second coil can be used to excite nearby anatomy more efficiently than the WBC because the second coil is smaller and closer to the nearby anatomy than the WBC. Compared to the first approach using a direct connection with wires, the inductive coupling approach may be less efficient than direct wiring but is still more efficient than a conventional WBC. One benefit of the inductive coupling approach is that no special wiring is required. However, conventional inductive coupling approaches require the use of multiple coils. For example, a conventional inductively coupled knee coil uses two layers of RF coils. The first (inner) layer includes a plurality of Rx coil elements which detect signals from the anatomy while operating in Rx mode, and which are decoupled from the transmitting field while operating in Tx mode. The second (outer) layer is typically a standard birdcage coil that inductively couples to a WBC to create a local amplified transmitting field in Tx mode and which is disabled in Rx mode. However, this conventional inductively coupled dual layer coil has drawbacks. For example, all the individual Rx coil elements in a conventional dual layer coil need associated circuits for decoupling the Rx coil and the local Tx coil while operating in Tx mode. Conventional inductively coupled dual layer coils also require circuits for switching off the Tx coil while operating in Rx mode, which requires complex and expensive control circuitry. This leads to complex and expensive coils. These multiple decoupling circuits and complex control circuits can also decrease the signal to noise ratio (SNR), thereby reducing image quality. Furthermore, the outer layer, by its proximity to the inner layer, will create additional noise when the inner layer is operating in Rx mode. Thus, conventional approaches to mitigating unwanted RF heating of guidewires in iMRI procedures, and the coils used therein, are suboptimal.

DETAILED DESCRIPTION

Embodiments described herein generate an amplified local Tx field using inductive coupling between a WBC and a local single-layer MRI RF coil array in which the magnitude or phase of an induced current in individual coil array elements of the local single-layer MRI RF coil array are independently adjustable to mitigate RF heating of an iMRI guidewire. Embodiments adjust the magnitude and phase of the induced current in individual coil array elements independently to vary the uniformity of the Tx field such that guidewire heating is mitigated during an iMRI procedure while image quality is maintained at a clinically useful level. A discussion of exemplary single layer MRI RF coils and RF coil array elements suitable for use by embodiments described herein now follows.

Figure 1:
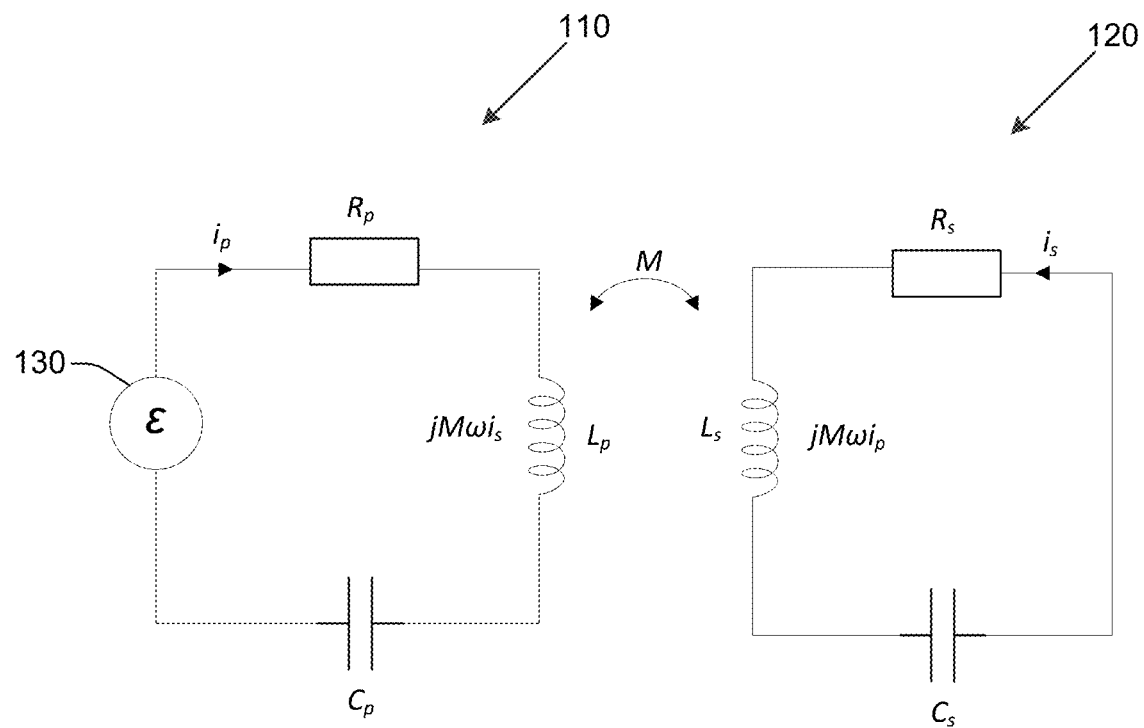
FIG. 1 illustrates inductively coupled resonant RF coils.

FIG. 1 illustrates an RF coil 110 and an RF coil 120. Coil 110 and coil 120 are resonant RF coils and are inductively coupled to each other. Coil 110 and coil 120 may be part of an MRI system or iMRI system. In this example, coil 110 operates as a primary coil and is driven by RF amplifier ε 130. Coil 120 operates as a secondary coil. Secondary coil 120 is inductively coupled to the primary coil 110 by mutual inductance M. Secondary coil 120 is driven by the mutual inductively coupled RF power from the primary coil 110. The primary coil 110 is, in this example, a WBC, while the secondary coil 120 is a local inductively coupled smaller coil. For the primary coil 110, $R_p$, $C_p$, and $L_p$ are defined as the coil loss resistance, the equivalent coil breaking point capacitance, and the equivalent total coil inductance respectively. The RF amplifier ε 130 is defined as an equivalent RF voltage source from an RF power amplifier through a matching circuit, which is not illustrated for clarity. The resistive loss from the RF amplifier ε 130 is absorbed by $R_p$, which may be pre-defined for simplicity of calculation. The mutual inductance between primary coil 110 and secondary coil 120 is defined as M. The resistive loss, the equivalent breaking point capacitance, and the total inductance of secondary RF coil 120 are defined as $R_s$, $C_s$, and $L_s$ respectively. The RF current through primary coil 110 is defined as $i_p$, and the RF current through secondary coil 120 is defined as $i_s$. Mutual inductance between primary RF coil 110 (e.g. $L_p$) and secondary RF coil 120 (e.g. $L_s$) generates an induced voltage on primary coil 110 $L_p$, which may be expressed as $+/-j\omega M i_s$. The sign of $j\omega M i_s$ is determined by the polarity between primary coil 110 and secondary coil 120. For clarity of exposition, the positive sign is used in this example. Similarly, the mutual inductance between secondary coil 120 and primary coil 110 generates an induced voltage on secondary coil 120, which may be expressed as $+/-j\omega M i_p$. The sign is the same for both primary coil 110 and secondary coil 120.

Using Kirchhoff's law, primary coil 110 and secondary coil 120 represented in FIG. 1 may be described by equation 1 below:

for primary coil 110: $Z_p i_p + j\omega M i_s = \varepsilon$ for secondary coil 120: $j\omega M i_p + Z_s i_s = 0$ \hfill (Eq. 1), where $$Z_p = R_p + j\left(\omega L_p - \frac{1}{\omega C_p}\right) \text{ and } Z_s = R_s + j\left(\omega L_s - \frac{1}{\omega C_s}\right),$$

where Z represents impedance.

Equation 1 may be re-written in matrix format, resulting in:

$$\begin{pmatrix} Z_p & j\omega M \\ j\omega M & Z_s \end{pmatrix} \begin{pmatrix} i_p \\ i_s \end{pmatrix} = \begin{pmatrix} \varepsilon \\ 0 \end{pmatrix} \quad \text{(Eq. 2)}$$

Thus, the solution to equation 2 is:

$$\begin{pmatrix} i_p \\ i_s \end{pmatrix} = \frac{1}{Z_p Z_s + \omega^2 M^2} \begin{pmatrix} Z_s \varepsilon \\ -j\omega M \varepsilon \end{pmatrix} \quad \text{(Eq. 3)}$$

where $$i_p = \frac{Z_s \varepsilon}{(Z_p Z_s + \omega^2 M^2)} \text{ and } i_s = \frac{-j\omega M \varepsilon}{(Z_p Z_s + \omega^2 M^2)}.$$

If both the primary coil 110 and the secondary coil 120 resonate at the same frequency, then $Z_p = R_p$ and $Z_s = R_s$. Thus $$i_p = \frac{R_s \varepsilon}{(R_p R_s + \omega^2 M^2)} \text{ and } i_s = \frac{-j\omega M \varepsilon}{(R_p R_s + \omega^2 M^2)}.$$

Recall that the phase of $i_s$ is opposite to the phase of $i_p$, per Lenz's Law. The ratio between $i_s$ and $i_p$ is $-j\omega M/R_s$. The secondary coil 120's quality factor (Q) may be high, i.e., the value of $R_s$ may be small. Therefore the ratio between current $i_s$ and $i_p$ may be large. Furthermore, because secondary coil 120 is smaller than primary coil 110 and is also closer to the imaging area than primary coil 110, the same magnitude of RF current generates a larger magnetic transmitting field at the area being imaged. Thus, a local inductive coil is significantly more power efficient than a large WBC coil and the local inductive coil's current is dominant compared to the primary coil's current even though their phases are opposite to each other. Furthermore, if a local inductive coil such as secondary coil 120 does not resonate at the frequency of primary coil 110, then the induced current $i_s$ in secondary coil 120 can be written as:

$$i_s = \frac{-j\omega M \varepsilon}{\left( R_p R_s + \omega^2 M^2 + jR_p \left( \omega L_s - \frac{1}{\omega C_s} \right) \right)} \quad \text{(Eq. 4)}$$

As shown in Eq. 4, the frequency deviation of secondary coil 120 from primary coil 110 can reduce the magnitude of $i_s$ and change the phase of $i_s$. This approach may be used by embodiments described herein to reduce the local coil 120's RF power efficiency if a particular MRI application requires it. For example, as demonstrated by Eq. 4, the induced current $i_s$ is a function of a coil loss resistance of primary coil 110, a coil loss resistance of secondary coil 120, or a difference between a working frequency of primary coil 110 and a resonant frequency of secondary coil 120. Thus, embodiments described herein may independently adjust a magnitude of the induced current in a local coil (e.g. secondary coil 120), or a phase of the induced current in a local coil (e.g. secondary coil 120) by adjusting the coil loss resistance of the primary coil (e.g. primary coil 110), the coil loss resistance of the secondary coil (e.g. secondary coil 120), or the difference between the working frequency and the resonant frequency. Embodiments described herein may therefore also adjust the magnitude of local Tx field generated by a single layer MRI RF coil operating in Tx mode.

Embodiments described herein include a single-layer MRI RF coil array that employs a single-layer approach to achieve a local inductively coupled Tx transmitter from a plurality of Rx receivers. An example single-layer MRI RF coil array may operate in a Tx mode or an Rx mode. In Rx mode the single-layer MRI RF coil array functions as a plurality of Rx receivers. In Tx mode multiple PIN diodes may be used to re-configure all or less than all the plurality of Rx receivers so that either all or less than all of the plurality of Rx receivers may inductively couple to the WBC and amplify the transmit field. Under this single-layer approach there are multiple approaches that may be employed by embodiments described herein to create a Tx field with a local inductively coupled coil.

Figure 2:
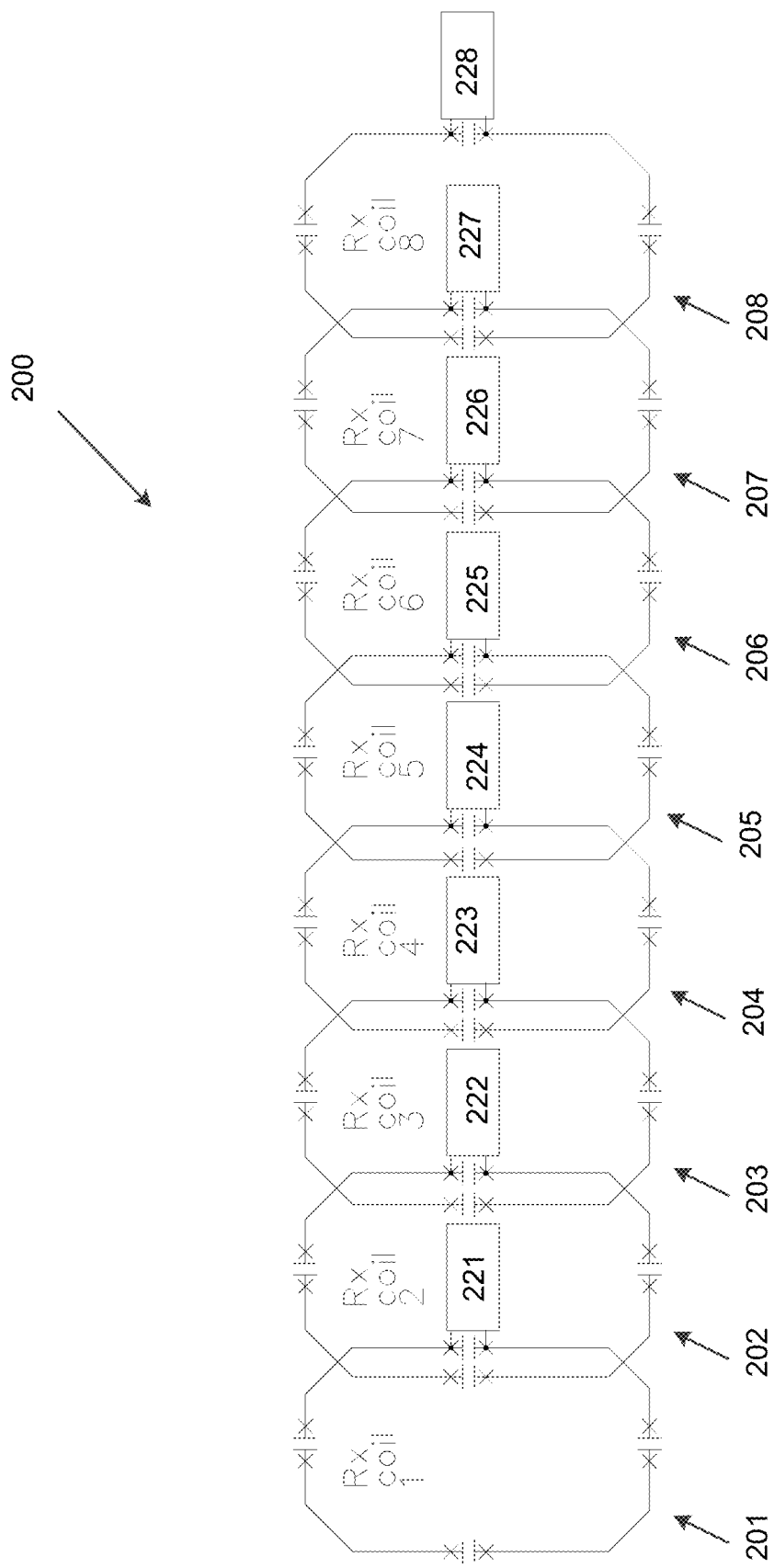
FIG. 2 illustrates a circuit diagram of an eight-rung birdcage coil.

A first single-layer approach is to use PIN diodes to configure a plurality of Rx coils together to create a local volume coil, such as a birdcage coil, and to inductively couple the local volume coil to a larger WBC. This first approach may be demonstrated by an example Rx coil that includes 8 loops configured as independent receivers on a cylindrical former. In examples described herein, a loop is considered to be an RF coil element, or RF coil array element. FIG. 2 is a diagram of an example 8-loop coil 200 in Rx mode. 8-loop coil 200 includes loops 201-208. In this example, a loop serves as an independent receiver, and includes receive electronics 221-228 respectively. Between directly neighboring loops (e.g. loops 202, 203, 204), the directly neighboring loops overlap each other to achieve good isolation, i.e., minimum mutual inductance. Good isolation between loops can also be achieved by using capacitors.

Figure 3:
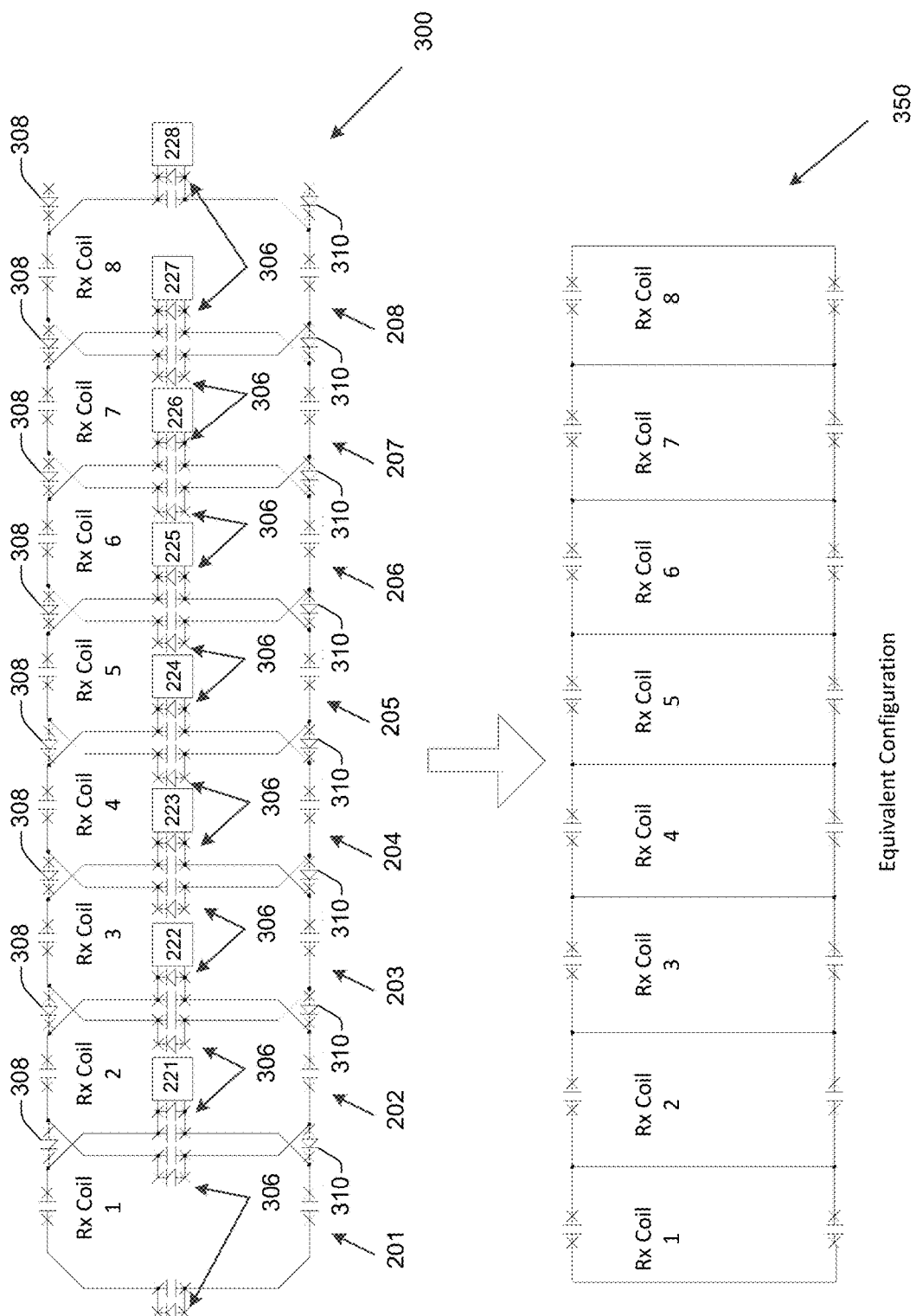
FIG. 3 illustrates a circuit diagram of an eight-rung birdcage coil and equivalent circuit.

FIG. 3 illustrates an Rx coil 300 that is similar to Rx 8-loop coil 200 illustrated in FIG. 2, but with additional elements and details. Rx coil 300 includes multiple PIN diodes 306, 308, and 310. A PIN diode has low impedance (e.g. is shorted) when it is forward biased by a DC power supply. In Tx mode the PIN diodes 306, 308, and 310 are forward biased. The circuitry supporting the PIN diodes 306, 308, and 310, such as RF chokes, is not illustrated in FIG. 3 for clarity. If all PIN diodes 306, 308, and 310 are shorted due to the application of a forward bias, then the circuit of the coil 300 is changed to the equivalent circuit 350. The equivalent circuit 350 illustrates an 8-rung birdcage coil that will inductively couple to a WBC in Tx mode and amplify the transmitting field and increase the efficiency of the WBC. In summary, the first approach of single-layer technology uses PIN diodes to reconfigure all or some of the Rx coil elements in a plurality of Rx coil elements into a local volume coil to increase WBC efficiency using inductive coupling, and to electrically link Rx coil elements together as one larger inductively coupled Tx coil. This first, conventional approach may be sub-optimal for two reasons. A first reason is that many diodes are required to link different Rx coils together. This increases the complexity of the coils. Therefore, this first, conventional approach may be expensive. The other reason is that even though PIN diodes are considered to be shorted when a forward bias is applied to the PIN diodes, the resistive losses of the PIN diodes are not trivial. A typical value of a forward biased PIN diode is 0.5 Ohm. This 0.5 Ohm could be larger than the coil loss itself for some high Q coils. This additional PIN diode resistive loss reduces the local inductively coupled RF coil's power efficiency.

Example embodiments described herein employ a second, different single-layer approach that uses PIN diodes to facilitate switching an Rx coil element into Tx mode so that all or part of all the Rx elements in a plurality of Rx elements can inductively couple to a WBC individually. In this approach, unlike in the first conventional approach, there are no PIN diodes between Rx elements (e.g., loops, RF coil elements) to link the Rx elements together. When forward-biased, a PIN diode may produce a negligible resistance (e.g., ~0.1Ω), which is essentially a short-circuit. When reverse-biased, a PIN diode may produce a high resistance (e.g., ~200 kΩ) in parallel with a low capacitance (e.g., ~2 pF), which is essentially an open-circuit.

An analysis of the induced current in the Rx elements of an array when operating in Tx mode illustrates the operation of the second approach employed by embodiments described herein. In this analysis it is assumed that the couplings among Rx elements are small and can be ignored. The couplings between Rx elements and the WBC are dominant. For example, the WBC field will induce voltage in one element and generate current flow in that element. That current flow will generate its own field. This additional field will induce voltage on this element's neighbors, including direct or indirect neighbors. This additional induced voltage is ignored in this analysis for clarity of exposition because of the assumption that the couplings among Rx elements are small.

Figure 4:
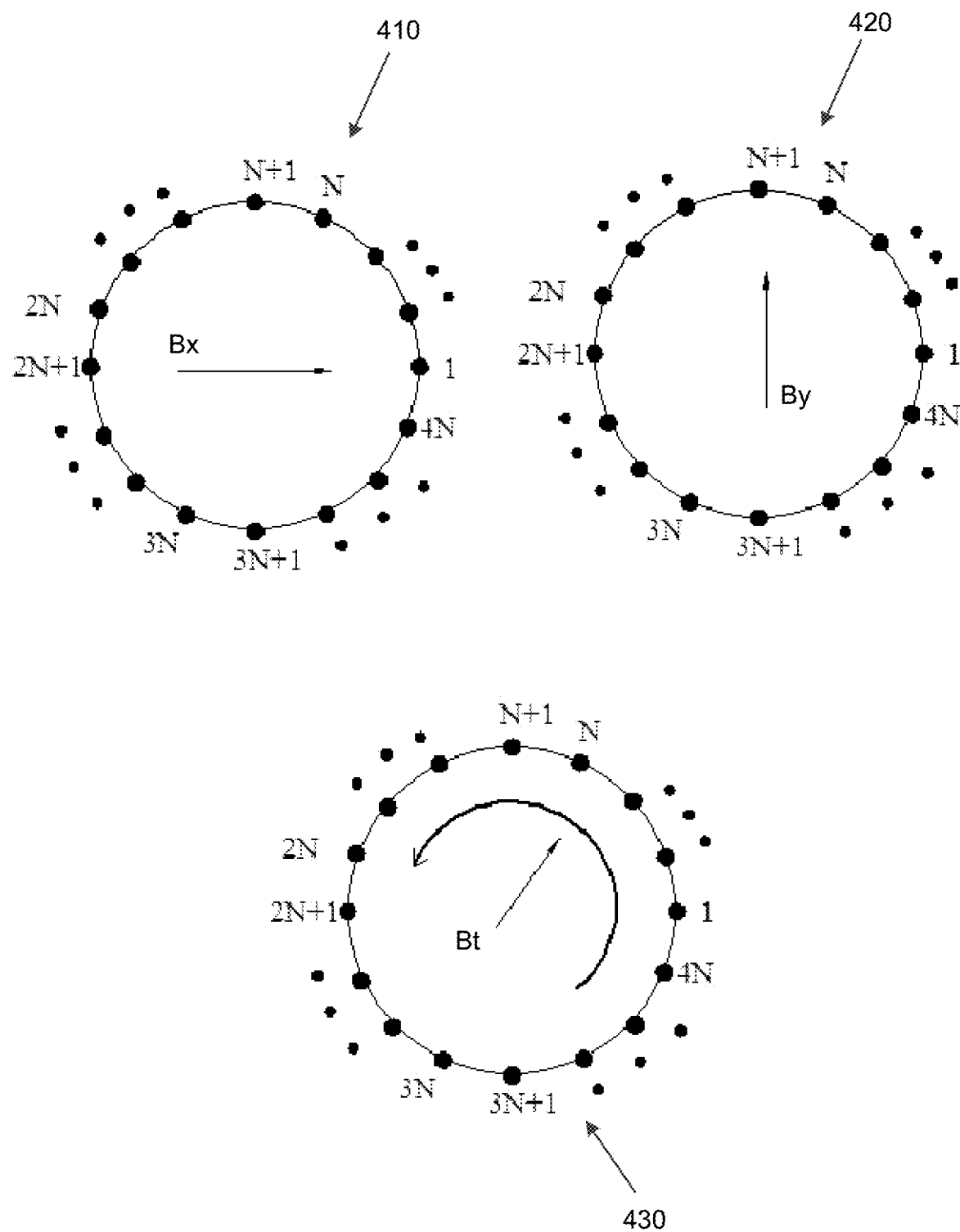
FIG. 4 illustrates current distribution through a birdcage coil.

FIG. 4 illustrates current distribution through rungs of a 4N-rung birdcage coil in circular polarized (CP) mode. Current distribution for a B field in the horizontal direction ($B_x$) is illustrated at 410. For a B field in the horizontal direction ($B_x$) the current through a rung k can be written as:

$$I_{kx} = I_0 \sin\left(\frac{2\pi}{4N}k\right)\sin(\omega_0 t) \quad \text{(Eq. 5)}$$

where k is the rung number (k=1, . . . , 4N) and $\omega_0$ is the working frequency.

Current distribution for a B field in the vertical direction ($B_y$) is illustrated at 420. For a B field in the vertical direction ($B_y$) the current through a rung k can be written as $$I_{ky} = \pm I_0 \cos\left(\frac{2\pi}{4N}k\right)\cos(\omega_0 t) \quad \text{(Eq. 6)}$$

For current distribution for a B field in the vertical direction ($B_y$), the time domain function is cosine instead of sine due to the circular polarized mode requirement. Furthermore, the "±" symbol indicates that the direction of $B_y$ may be upward or downward. This affects the rotational direction of the final circular polarized B field, illustrated at 430, by making the final circular polarized B field rotate either clockwise or counterclockwise. The total current through a rung k is the sum of the two currents described in equation 5 and equation 6. Therefore:

$$I_k = \quad \text{(Eq. 7)}$$
$$I_0 \sin\left(\frac{2\pi}{4N}k\right)\sin(\omega_0 t) \pm I_0 \cos\left(\frac{2\pi}{4N}k\right)\cos(\omega_0 t) = I_0 \cos\left(\omega_0 t \pm \frac{2\pi}{4N}k\right)$$

In this example, a first rung has the same current magnitude $I_0$ and angular frequency $\omega_0$ as another, different rung. The currents in different rungs differ with respect to phase. Thus, a typical high pass, low pass, or bandpass WBC's current distribution in its rungs can be described by Eq. 7.

Figure 5:
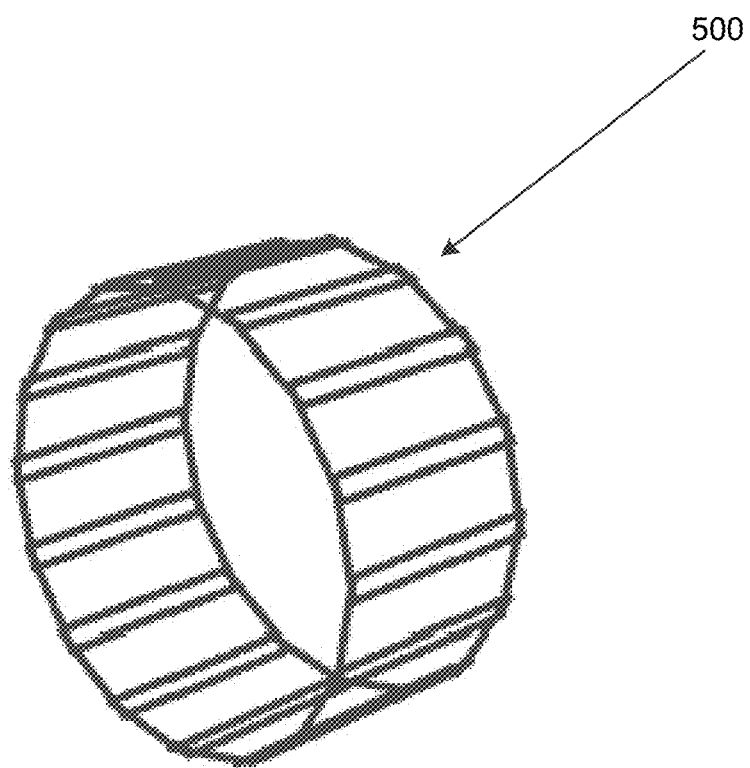
FIG. 5 illustrates an example birdcage coil.

Consider a 4N loops Rx coil that is put inside this circular polarized uniform B field, where the circular polarized uniform B field is generated by a birdcage coil or WBC. FIG. 4, element 430 illustrates current distribution for a B field generated from a birdcage coil or WBC in this situation. In this example, good isolation among all loops is assumed. Furthermore, in this example, each loop is identical, the loops use overlap to isolate the directly neighboring elements, all loops are in the same row, and the loops are wrapped around a cylindrical former. FIG. 5 illustrates an example 16 loop coil 500 configured as a birdcage coil.

In transmit mode the CP $B_1$ field from a birdcage coil (e.g. a WBC) induces voltage in each loop. The induced voltage for a loop can be written as $$V_{induced} = \frac{d(\vec{B_1}\cdot\vec{A_k})}{dt} \quad \text{(Eq. 8)}$$

where $\vec{A_k}$ is the area vector, where the magnitude is the area of the $k_{th}$ loop and the direction is the direction perpendicular to the area towards the outside of the coil.

The $B_1$ field and area vector $\vec{A_k}$ can be written as:

$$\vec{B_1} = B_1(\cos(\omega_0 t)\hat{x} + \sin(\omega_0 t)\hat{y}) \quad \text{(Eq. 9)}$$

$$\vec{A_k} = A_0\left(\cos\left(\frac{2\pi}{8N} + (k-1)*\frac{2\pi}{4N}\right)\hat{x} + \sin\left(\frac{2\pi}{8N} + (k-1)*\frac{2\pi}{4N}\right)\hat{y}\right) \quad \text{(Eq. 9a)}$$

where $A_0$ is the area of a loop. Loops in this example have identical dimensions and thus have the same areas. In particular embodiments, loops may have different areas, and calculations may be adjusted accordingly.

Then, equation 8 can be re-written as:

$$V_{induced} = A_0 B_1 \omega_0 \left(-\sin(\omega_0 t)\cos\left(\frac{2\pi}{8N} + (k-1)*\frac{2\pi}{4N}\right) + \right. \quad \text{(Eq. 10)}$$
$$\left. \cos(\omega_0 t)\sin\left(\frac{2\pi}{8N} + (k-1)*\frac{2\pi}{4N}\right)\right)$$
$$= A_0 B_1 \omega_0 \sin\left(\frac{2\pi}{8N} + (k-1)*\frac{2\pi}{4N} - \omega_0 t\right)$$

Therefore, the current through the equivalent $k_{th}$ rung position is $$I_{induced\_no\_coupling\_k} = \quad \text{(Eq. 11)}$$
$$\frac{V_k - V_{k-1}}{R} = \frac{A_0 B_1 \omega_0}{R} * 2 * \sin\left(\frac{2\pi}{8N}\right) * \cos\left((k-1)*\frac{2\pi}{4N} - \omega_0 t\right)$$

where R is the impedance of a loop. At the resonant frequency the reactive part of the impedance is self-cancelled and only the real part is left. As demonstrated by both equation 11 and equation 7, a uniform circular $B_1$ field results. The final $B_1$ field $B_t$ inside the loops is the sum of both. As a result the final $B_1$ field $B_t$ inside a small cylinder may be uniform.

In one embodiment, the isolations between coil elements are very small. If the isolations are not small and the mutual inductance is defined as $M_{kj}$ between the $k_{th}$ and $j^{th}$ elements, high order coupling among elements may be ignored, and thus:

$$V_{kj} = M_{kj}\frac{d(I_j)}{dt} \quad \text{(Eq. 12)}$$

Therefore, the $k_{th}$ element will see additional coupled voltage from the $j_{th}$ element.

Summing all of the coupled voltages of the $k_{th}$ element results in:

$$V_k = A_0 B_1 \omega_0 \sin\left(\frac{2\pi}{8N} + (k-1)*\frac{2\pi}{4N} - \omega_0 t\right) - \sum_{j=1 \text{ and } j \neq k}^{4N} \left(M_{kj} * A_0 B_1 \omega_0^2 \cos\left(\frac{2\pi}{8N} + (j-1)*\frac{2\pi}{4N} - \omega_0 t\right)\right) \quad \text{(Eq. 13)}$$

Taking the same approach as illustrated in equation 11, then the induced current at the kth rung position can be written as $$I_{induced\_coupled\_k} = I_{induced\_no\_coupling\_k} - \sum_{j=1 \text{ and } j \neq k \text{ or } j \neq k-1}^{4N} \left((M_{kj} - M_{(k-1)j}) * A_0 B_1 \omega_0^2 \cos\left(\frac{2\pi}{8N} + (j-1)*\frac{2\pi}{4N} - \omega_0 t\right)\right) / R \quad \text{(Eq. 14)}$$

As demonstrated by equation 14 above, the second term in the right side of equation 14 still creates a uniform $B_1$ field. Therefore, compared to the non-coupled case described in equation 11, the coupled case still creates a uniform $B_1$ field. The difference here is that the couplings create the coupled $B_1$ field which makes the whole coil array less power efficient than the non-coupled case. However, as long as this uniform coupled field is still more efficient than the primary coil, (i.e., the WBC) the coil elements may still be used to resonate to improve RF power efficiency and reduce SAR.

Figure 6:
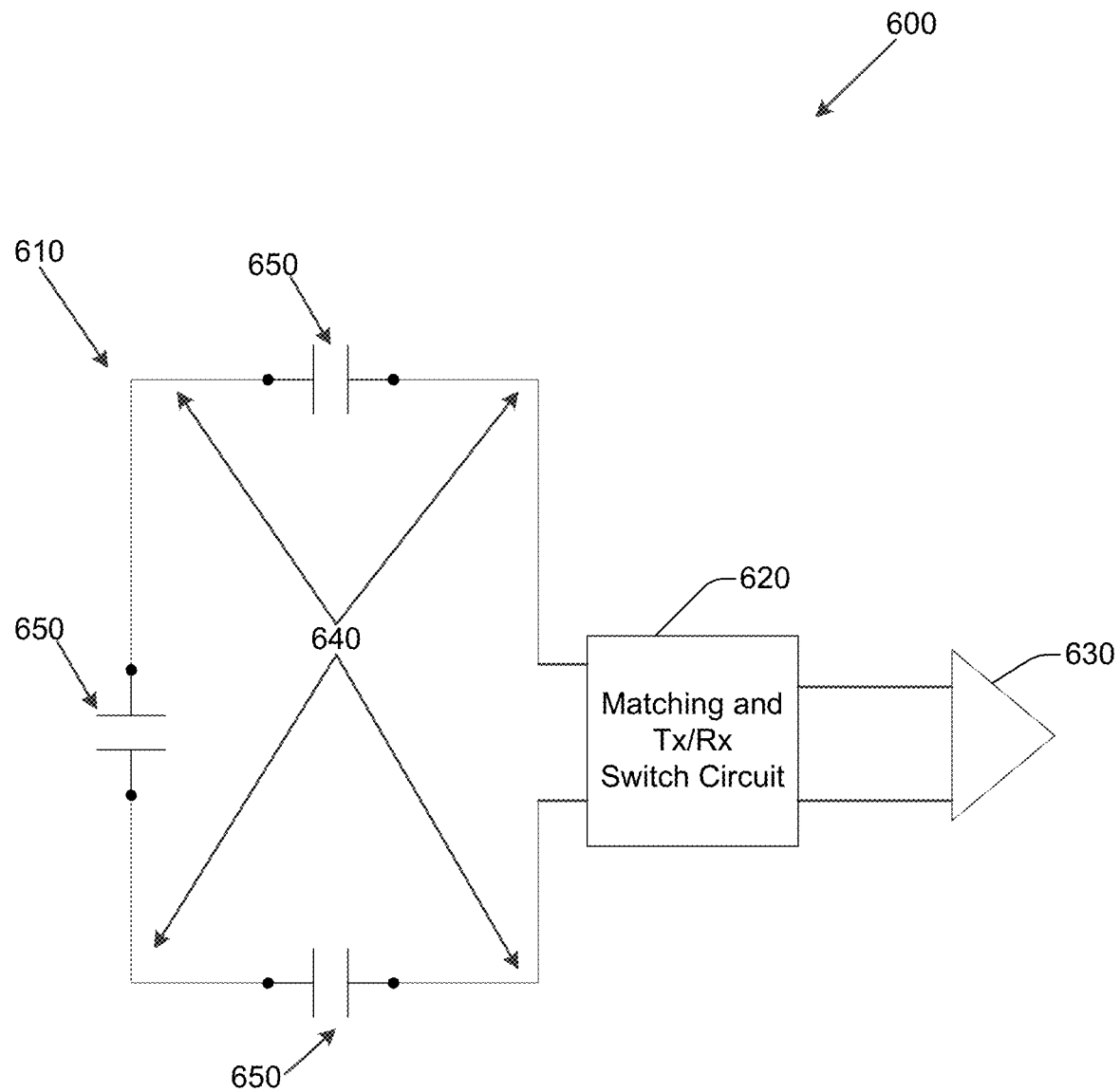
FIG. 6 illustrates an example single-layer MRI RF coil element.

FIG. 6 illustrates an example embodiment of an MRI RF coil element 600 that may be part of a single-layer MRI RF coil array, and that may be used in an iMRI procedure. MRI RF coil element 600 employs the second approach to generate a local Tx field. In FIG. 6, the configuration illustrated includes one Rx element only, for clarity. Employing a MRI RF coil element 600 as part of a single-layer MRI RF coil array using the second approach is simpler than the first approach because fewer PIN diodes are required to switch between Tx mode and Rx mode. Example embodiments thus improve on conventional approaches by saving space within the bore of an MRI apparatus because less hardware is used to construct example embodiments, by avoiding electromagnetic (EM) interference that may be caused by unnecessary hardware, and by reducing manufacturing costs by requiring less hardware, including PIN diodes, than conventional approaches. Example embodiments therefore offer at least one measurable improvement on conventional approaches in addition to providing improved SNR and more uniform fields.

FIG. 6 illustrates an MRI RF coil element 600 configured to operate in a transmit (Tx) mode or in a receive (Rx) mode. In one embodiment, MRI RF coil element 600 may be part of a single-layer MRI RF coil array configured for use in an iMRI system. A single-layer MRI RF coil array comprises at least one RF coil element (e.g., MRI RF coil element 600). The single-layer MRI RF coil array may be arranged in an anatomy-specific shape or configuration, including a closed-shape configuration (e.g. a birdcage coil), or arranged in an open-shape configuration (e.g. in a "C" or "U" shape), or other shaped configuration. In one embodiment, the single-layer MRI RF coil array may be a birdcage coil array. For example, FIG. 5 illustrates an example birdcage coil array 500. Birdcage coil array 500 is a sixteen loop, single-row coil array comprising sixteen MRI RF coils. A member of the sixteen MRI RF coils may be, for example, MRI RF coil element 600. In another embodiment, an element of the single-layer MRI RF coil array is configured in a saddle-like configuration. In another embodiment, a first element of the single-layer MRI RF coil array is configured in a saddle-like configuration, while a second, different element of the single-layer MRI RF coil array is configured as a loop.

The at least one RF coil element 600 includes an LC coil 610, a matching and Tx/Rx switch circuit 620, and a preamplifier 630. LC coil 610 includes at least one inductor 640 and at least one capacitor 650. The at least one inductor 640 and the at least one capacitor 650 resonate at a first frequency (i.e., a resonant frequency). The at least one inductor 640 may be, for example, a co-axial cable, a copper wire, a copper foil soldered to a circuit board, or other conductor.

RF coils for MRI may need to be tuned and matched. Tuning involves establishing or manipulating the capacitance in a coil so that a desired resistance is produced. Matching involves establishing or manipulating the capacitance in a coil so that a desired reactance is achieved. When tuning, the impedance z may be described by $Z=R+jX=1/(1/(r+jL\omega)+jC\omega)$. Tuning may be performed to achieve a desired tuning frequency for a coil. $\omega_0$ identifies the desired tuning frequency. $\omega_0$, may be, for example, 63.87 MHz at 1.5 T. The size of a conventional coil facilitates estimating inductance L. With an estimate of L in hand, values for capacitors can be computed to produce a desired resonant peak in an appropriate location with respect to $\omega_0$. Once capacitors are selected, the resonant peak can be observed and a more accurate L can be computed. The capacitors can then be adjusted to produce the desired resistance. Once the desired resistance is achieved, then capacitance can be adjusted to cancel reactance.

The matching and Tx/Rx switch circuit 620, when operating in Tx mode, electrically isolates the LC coil 610 from the preamplifier 630 upon the LC coil 610 resonating with a primary coil (not illustrated) at a working frequency of the primary coil. The matching and Tx/Rx switch circuit 620 electrically isolates the LC coil 610 from the preamplifier 630 by providing a threshold level of impedance between the LC coil 610 and the preamplifier 630. The primary coil may be, for example, a WBC or other primary coil that is larger than RF coil element 600. The LC coil 610, upon resonating with the primary coil at the working frequency, generates a local amplified Tx field based on an induced current in the LC coil 610. The induced current has a magnitude and a phase. The magnitude of the induced current or the phase of the induced current may be independently adjustable. For example, the induced current is a function of at least a coil loss resistance of the WBC, a coil loss resistance of the LC coil 610, or a difference between a working frequency of the WBC and a resonant frequency of the LC coil 610. In this embodiment, the frequency of the induced current is the same as the working frequency of the current in the primary coil or WBC, even though the resonant frequency of the LC coil 610 may be different. Embodiments described herein facilitate adjusting the coil loss resistance of the WBC, the coil loss resistance of the LC coil 610, or the difference between the working frequency of the WBC and the resonant frequency of the LC coil 610. The magnitude of the induced current or the phase of the induced current are configured to be varied over a range of magnitudes or phases respectively. Example embodiments thus facilitate independently adjusting the magnitude of an induced current in LC coil 610, or a phase of the induced current.

Matching and Tx/Rx switch circuit 620, when operating in Rx mode, electrically connects the LC coil 610 with the preamplifier 630 by providing low impedance between the LC coil 610 and the preamplifier 630. Preamplifier 630 may be a low input impedance low noise amplifier (LNA). In one embodiment, matching and Tx/Rx switch circuit 620 may be a capacitive matching and Tx/Rx switch circuit. In another embodiment, matching and Tx/Rx switch circuit 620 may be an inductive matching and Tx/Rx switch circuit.

Figure 7:
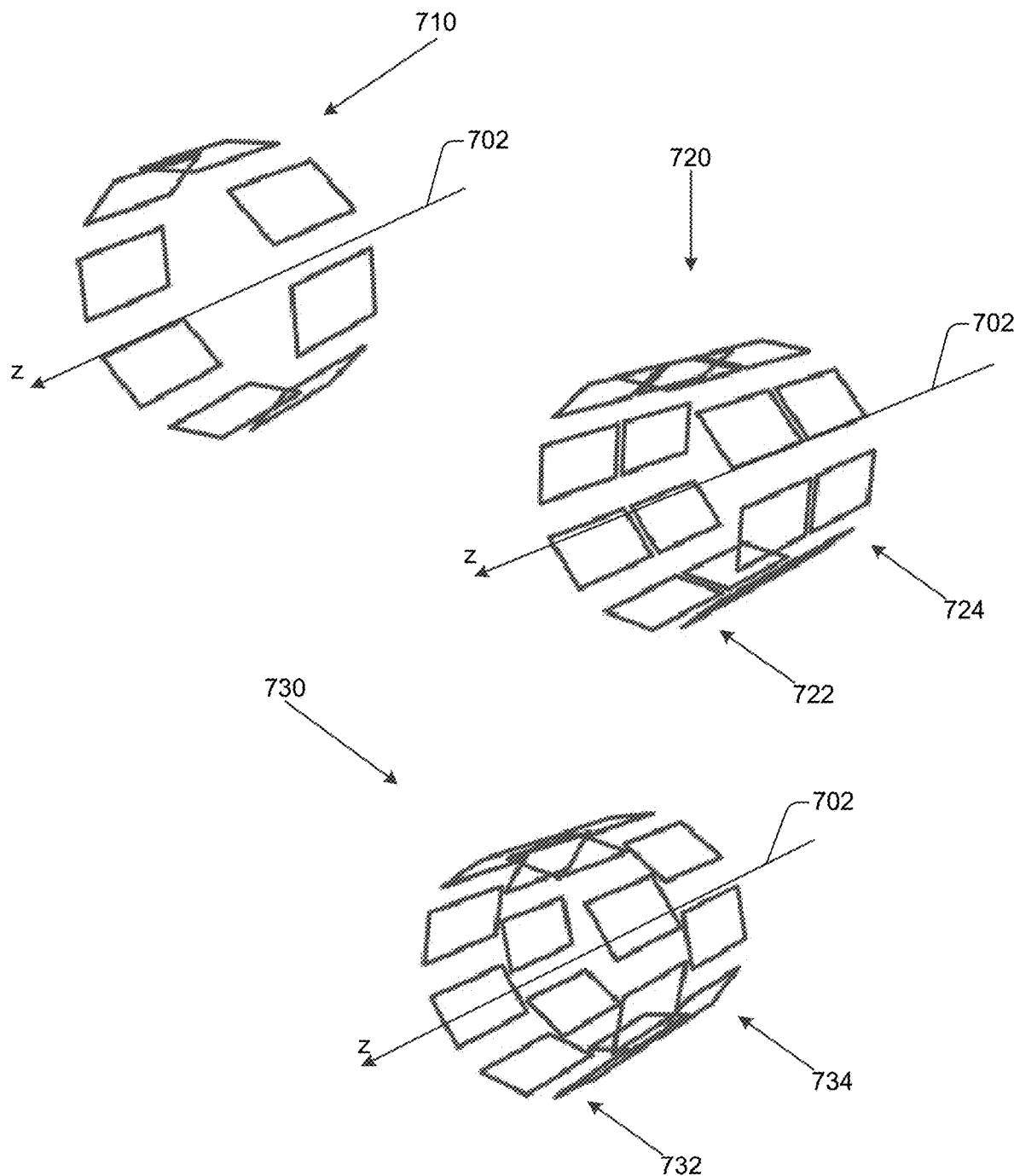
FIG. 7 illustrates an example single-layer MRI RF coil arrays.

Example MRI RF coil elements, MRI RF coil arrays, MRI RF coils, apparatus, and other embodiments, may be configured, for example, as bird cage coils. FIG. 7 illustrates one embodiment of a single-layer MRI RF coil array 710 that includes at least one MRI RF coil elements arranged in a single-row birdcage configuration. The at least one MRI RF coil elements may include, for example, MRI RF coil element 600, 800, 900, 1000, 1100, 1200, or 1500. FIG. 7 also illustrates an example embodiment of a single-layer MRI RF coil array 720 that includes at least one example MRI RF coil elements arranged in a two-row configuration. Single-layer MRI RF coil array 720 includes a first row 722 aligned with a second row 724. First row 722 includes at least four RF coil elements. Second row 724 includes at least four RF coil elements. FIG. 7 further illustrates another, single-layer MRI RF coil array 730. Single layer MRI coil array 730 is similar to single-layer MRI RF coil array 720, except the first row 732 is not aligned with second row 734. For example, first row 732 may be rotated a number of degrees around a central axis (e.g. z axis) shared with second row 734, while 734 is not rotated, or is rotated a different number of degrees. In different embodiments, first row 732 may be aligned to within a threshold level of alignment with second row 734.

In one embodiment, MRI RF coil array 720 includes a first plurality of RF coil elements (e.g. first row 722) and a second plurality of RF coil elements (e.g. second row 724). The first plurality of RF coil elements and the second plurality of RF coil elements are radially disposed about a longitudinal axis 702. The first plurality and the second plurality may be longitudinally offset a threshold distance greater than zero along the longitudinal axis 702. In one embodiment, an element of the first plurality of RF coil elements is axially offset a threshold amount from a respective element of the second plurality of RF coil elements. For example, an element of the first plurality of RF coil elements may be axially offset 15 degrees, 30 degrees, or another, different number of degrees, from a respective element of the second plurality of RF coil elements. The first plurality and the second plurality may include the same number of RF coil elements, or may include different numbers of RF coil elements. For example, in one embodiment, the first plurality may include eight RF coil elements, while the second plurality may include nine RF coil elements. Other, different numbers of RF coil elements may be employed.

In another embodiment, the at least one RF coil elements is arranged in a three-row configuration. For example, a three-row single layer MRI RF coil array may include a first row that includes at least five RF coil elements, a second row that includes at least five RF coil elements, and a third row that includes at least five RF coil elements. In this embodiment, the first row, second row, and third row may be aligned axially, or may be unaligned axially. In another embodiment, other different numbers of rows, number of RF coil elements, or combinations of alignments may be employed.

For example, in one embodiment, MRI RF coil array 720 includes a first plurality of RF coil elements 722, a second plurality of RF coil elements 724, and a third plurality of RF coil elements (not illustrated). In this embodiment, the first plurality of RF coil elements 722, the second plurality of RF coil elements 724, and the third plurality of RF coil elements are radially disposed about a longitudinal axis. The first plurality 722, the second plurality 724, and the third plurality are longitudinally offset a threshold amount along the longitudinal axis. In one embodiment, an element of the first plurality 722 of RF coil elements is axially offset a threshold amount from a respective element of the second plurality 724 of RF coil elements or the third plurality of RF coil elements. The first plurality 722, the second plurality 724, and the third plurality may include the same number of RF coil elements, or may include different numbers of RF coil elements. For example, in one embodiment, the first plurality 722 may include eight RF coil elements, the second plurality 724 may include nine RF coil elements, and the third plurality may include seven RF coil elements. In another embodiment, the first plurality 722, the second plurality 724, or the third plurality may include other, different numbers of RF coil elements.

Figure 8:
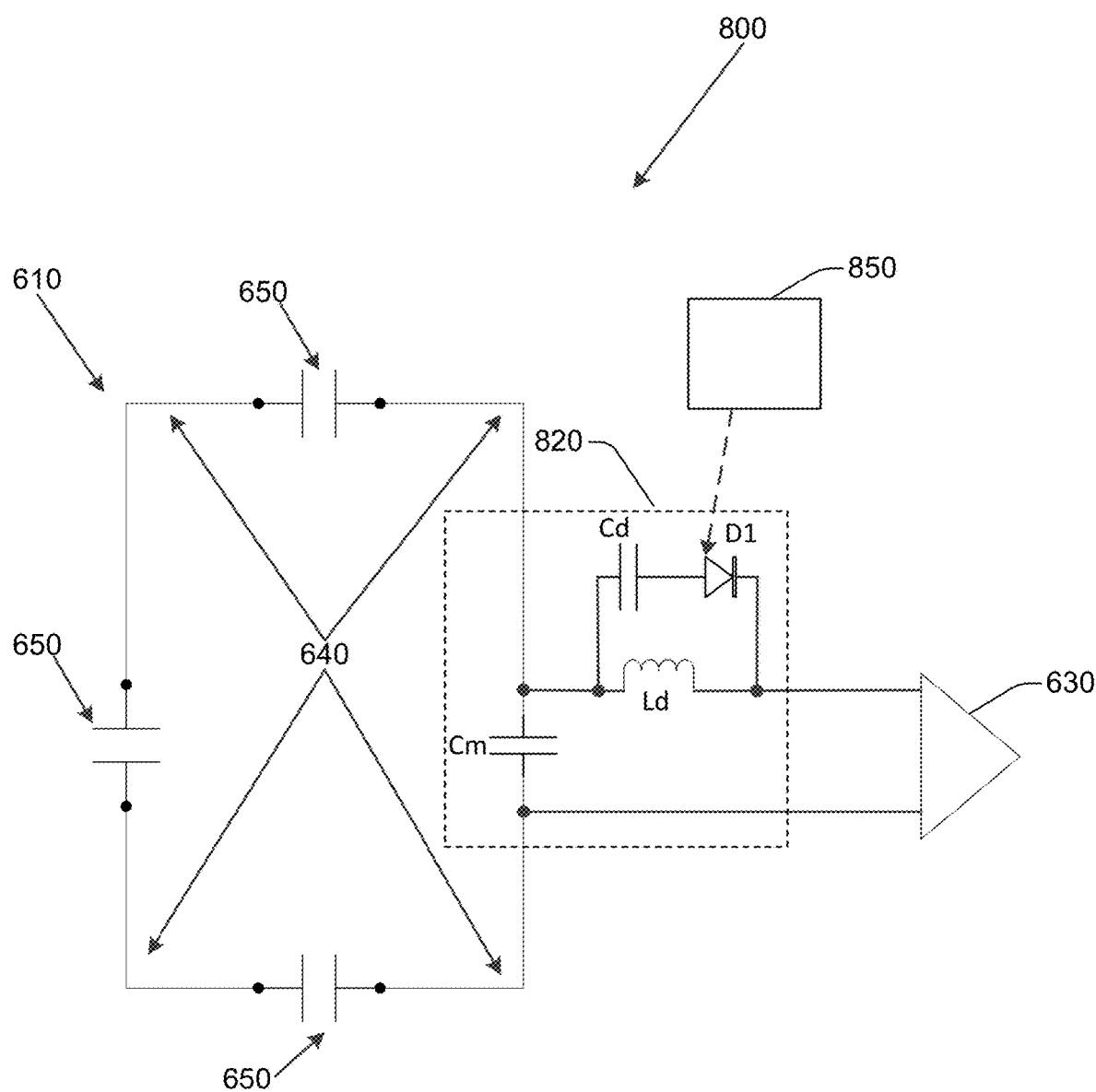
FIG. 8 illustrates an example single-layer MRI RF coil element.

FIG. 8 illustrates an MRI RF coil element 800. MRI RF coil element 800 is similar to MRI RF coil element 600, but includes additional elements and details. MRI RF coil element 800 may be part of a single-layer MRI RF coil array. The single-layer MRI RF coil array comprises at least one RF coil element 800. In one embodiment, MRI RF coil element 800 includes a matching and Tx/Rx switch circuit 820 configured to operate as a capacitive matching and Tx/Rx circuit. In this embodiment, matching and Tx/Rx switch circuit 820 includes a matching capacitor Cm, a first diode D1, a capacitor Cd, and a first inductor Ld. First diode D1 may be a PIN diode. The first diode D1, capacitor Cd, and first inductor Ld create a resonant tank circuit in Tx mode when first diode D1 is forward biased. This resonant tank circuit isolates input to the LNA preamplifier 630 from an induced high current or voltage in LC coil 610. The resonant tank circuit further facilitates LC coil 610, including capacitors 650, inductors 640, and matching capacitor Cm, to resonate at a high Q without preamplifier 630 being electrically connected to the RF coil.

In this embodiment, matching capacitor Cm has a first terminal and a second terminal. Matching capacitor Cm is connected, at a first terminal, to a first terminal of first inductor Ld. First inductor Ld is connected at a first terminal, to a capacitor Cd, at a first terminal. Capacitor Cd is connected, at a second terminal, to first diode D1, at a first terminal. First diode D1 is connected, at a second terminal to first inductor Ld, at a second terminal. First inductor Ld is connected, at a second terminal, to a first input terminal of preamplifier 630. Preamplifier 630 is connected, at a second input terminal, to the second terminal of matching capacitor Cm. In Rx mode, first diode D1 is backward biased (i.e, first diode D1 has a high impedance in Rx mode), so that effectively only Ld is presented between Cm and Preamplifier 630. While in this example first inductor Ld, first diode D1, and capacitor Cd are illustrated on a connection path between the first terminal of matching capacitor Cm and a first input terminal of preamplifier 630, in another embodiment, first inductor Ld, first diode D1, and capacitor Cd may be connected instead between the second terminal of matching capacitor Cm and the second input terminal of preamplifier 630.

In one embodiment, MRI RF coil element 800 further includes a PIN diode control circuit 850. PIN diode control circuit 850 facilitates selective control of first diode D1. For example, PIN diode control circuit 850 controls a forward bias applied to first diode D1. PIN diode control circuit 850 may be operably connected to, for example, first diode D1. In another embodiment, PIN diode control circuit 850 facilitates selective control of other, different diodes, including shunt diodes, or PIN diodes that comprise a magnitude/phase control component.

Figure 9:
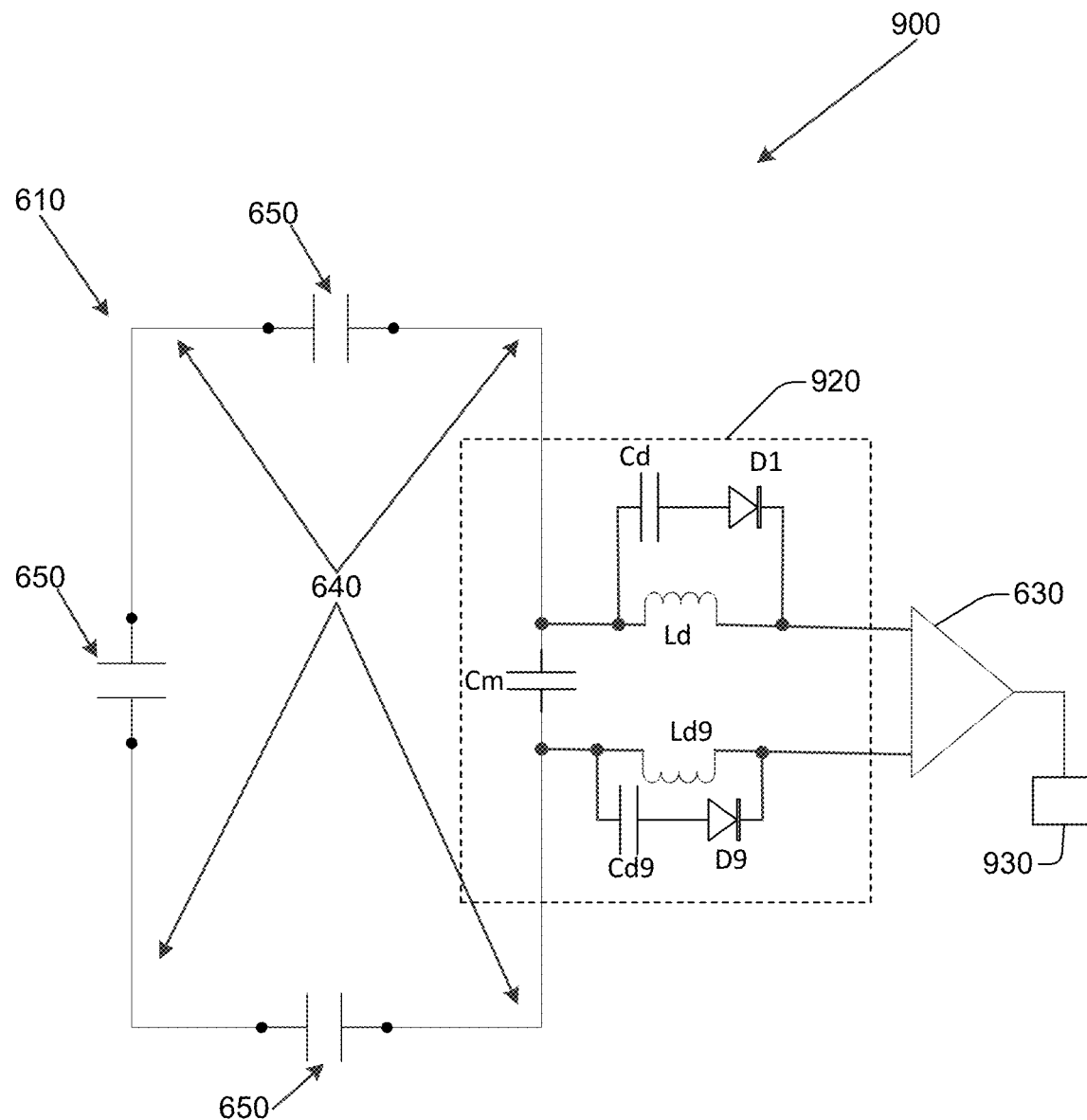
FIG. 9 illustrates an example single-layer MRI RF coil element.

FIG. 9 illustrates an MRI RF coil element 900. MRI RF coil element 900 is similar to MRI RF coil element 800, but includes additional elements and details. MRI RF coil element 900 includes matching and Tx/Rx switch circuit 920. In this embodiment, matching and Tx/Rx switch circuit 920 includes matching capacitor Cm, first diode D1, first capacitor Cd, and first inductor Ld. Matching and Tx/Rx switch 920 also includes second diode D9, second capacitor Cd9, and second inductor Ld9. Second diode D9 may be a PIN diode. The first diode D1, first capacitor Cd first inductor Ld, and second diode D9, second capacitor Cd9, and second inductor Ld9 create a resonant tank circuit in Tx mode when first diode D1 or second diode D14 is forward biased. This resonant tank circuit isolates input to preamplifier 630 from an induced high current or voltage in LC coil 610. The resonant tank circuit further facilitates LC coil 610, including capacitors 650, inductors 640, and matching capacitor Cm, resonating at a high Q without preamplifier 630 being electrically connected to the RF coil.

In this embodiment, matching capacitor Cm has a first terminal and a second terminal. Matching capacitor Cm is connected, at a first terminal, to a first terminal of first inductor Ld. First inductor Ld is attached at a first terminal, to first capacitor Cd, at a first terminal. First capacitor Cd is attached, at a second terminal, to first diode D1, at a first terminal. First diode D1 is attached, at a second terminal to a second terminal of first inductor Ld. First inductor Ld is connected, at a second terminal, to a first input terminal of preamplifier 630. Matching capacitor Cm is connected, at a second terminal, to a first terminal of second inductor Ld9. Second inductor Ld9 is connected, at a first terminal, to second capacitor Cd9, at a first terminal. Second capacitor Cd9 is connected, at a second terminal, to second diode D9, at a first terminal. Second diode D9 is connected, at a second terminal, to a second terminal of second inductor Ld9. Second inductor Ld9 is connected, at a second terminal, to a second input terminal of preamplifier 630.

In one embodiment, MR RF coil element 900 further includes a balun 930. In this embodiment, balun 930 is connected, at a first coaxial or two-connection terminal, to a first coaxial or two-connection output terminal of preamplifier 630. In another embodiment, balun 930 is connected between matching and Tx/Rx switch 920 and preamplifier 630. Balun 930 reduces a common mode current flowing in transmission lines that may connect MRI RF coil element 900 with an MRI system or iMRI system (not illustrated).

Figure 10:
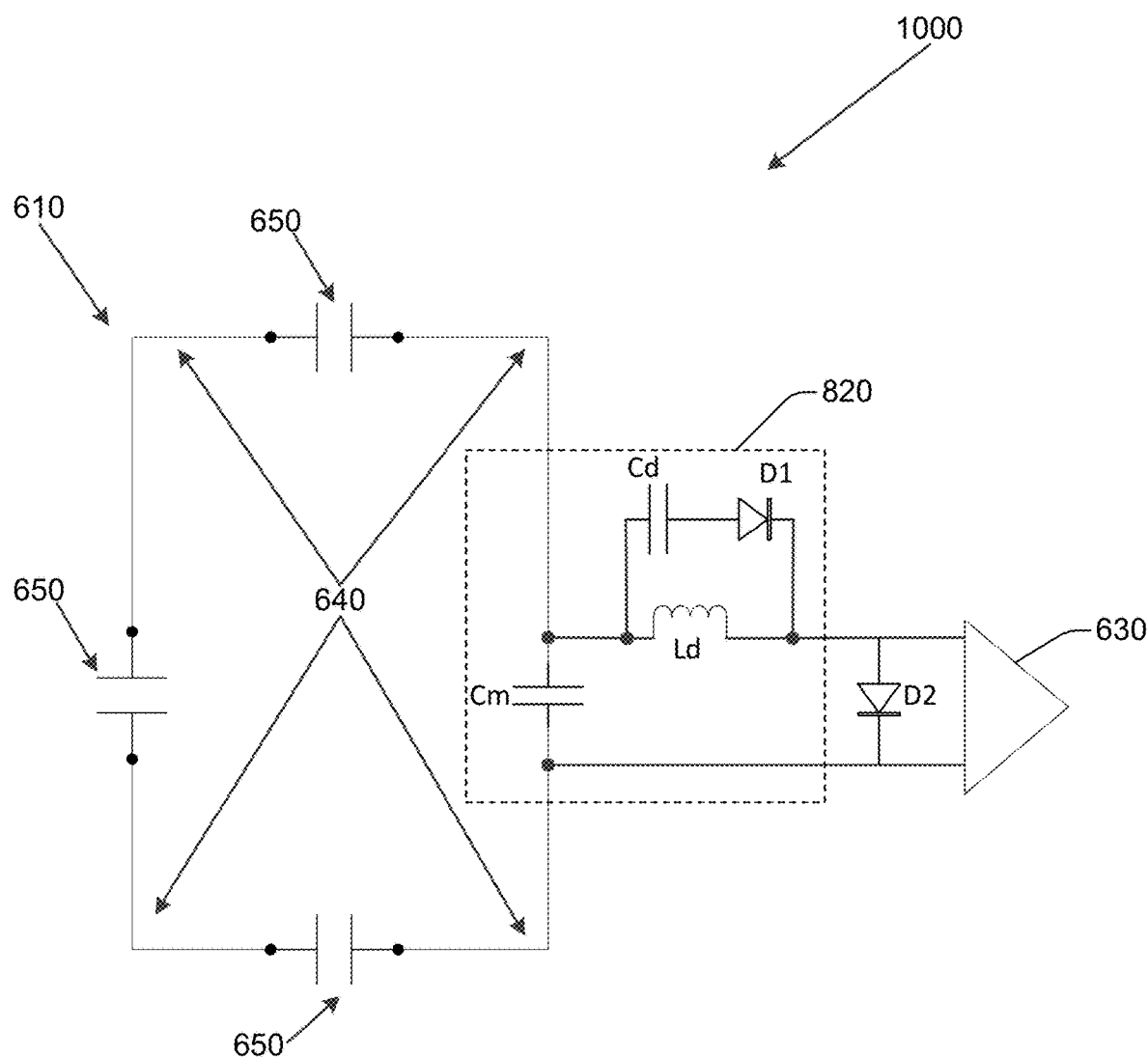
FIG. 10 illustrates an example single-layer MRI RF coil element.

FIG. 10 illustrates an MRI RF coil element 1000. MRI RF coil element 1000 is similar to MRI RF coil element 800, but includes additional elements and details. MRI RF coil element 1000 may be part of a single-layer MRI RF coil array. The single-layer MRI RF coil array comprises at least one RF coil element 1000. MRI RF coil element 1000 includes shunt diode D2. Shunt diode D2 may be a PIN diode. Shunt diode D2 has a first terminal and second terminal. Shunt diode D2 is connected, at a first terminal, to the first input terminal of preamplifier 630. Shunt diode D2 is connected, at a second terminal, to the second input terminal of pre-amplifier 630. To further improve isolation between high induced current in LC coil 610 and LNA preamplifier 630, shunt diode D2 provides additional shunt protection for the LNA preamplifier 630.

Figure 11:
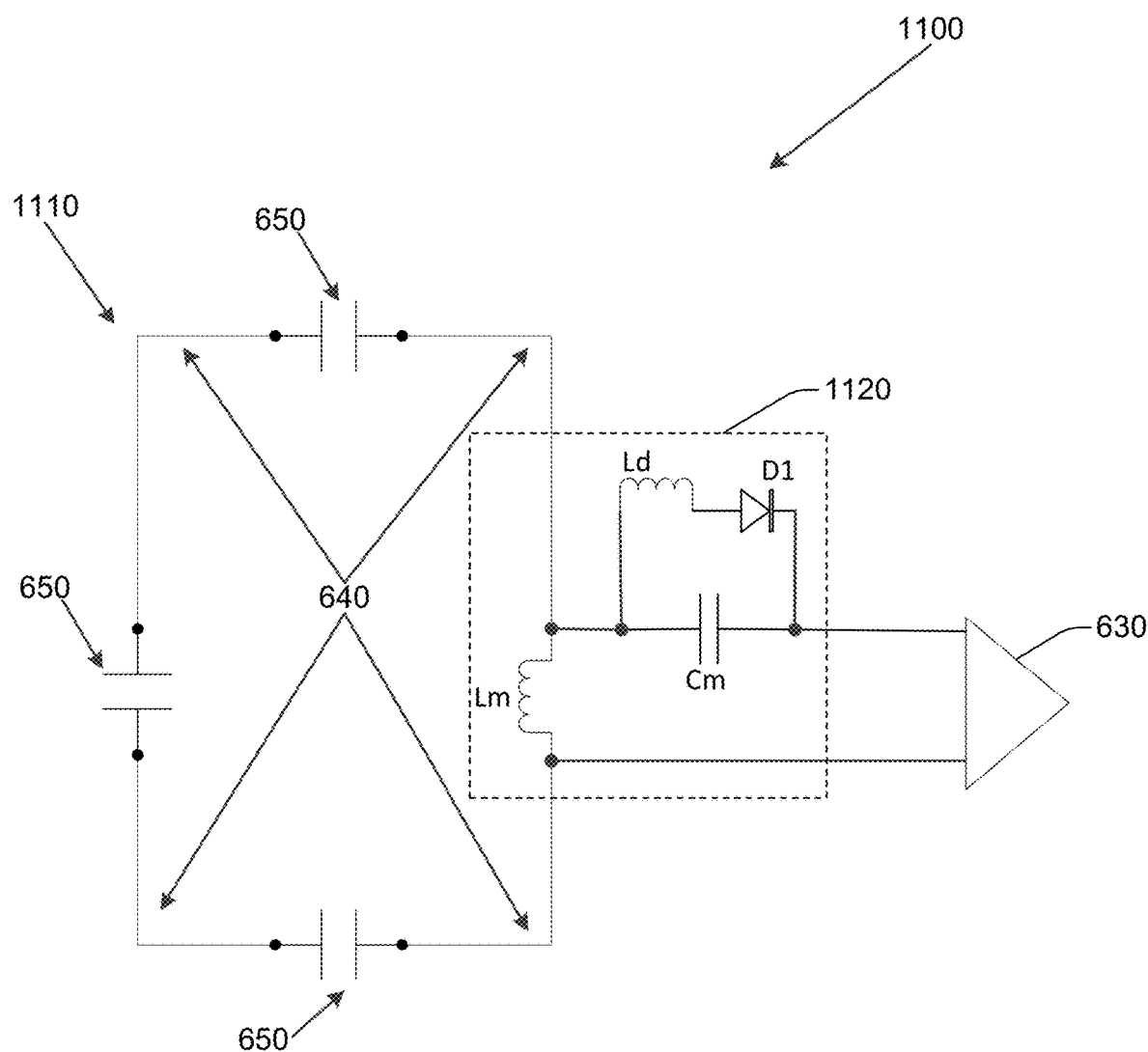
FIG. 11 illustrates an example single-layer MRI RF coil element.

FIG. 11 illustrates an MRI RF coil element 1100. MRI RF coil element 1100 is similar to MRI RF coil element 600, but includes additional elements and details. MRI RF coil element 1100 may be part of a single-layer MRI RF coil array. The single-layer MRI RF coil array comprises at least one RF coil element 1100. RF coil element 1100 includes an LC coil 1110. LC coil 1110 is similar to LC coil 610 but includes a matching inductor Lm having a first terminal and a second terminal. LC coil 1110 also includes at least one conductor 640 having a first end connected to the first terminal of the matching inductor Lm, and a second end connected to the second terminal of the matching inductor Lm.

In this embodiment, matching and Tx/Rx switch 1120 operates as an inductive matching circuit. Matching and Tx/Rx switch 1120 is connected to matching inductor Lm. Matching and Tx/Rx switch 1120 includes first inductor Ld having a first terminal and a second terminal, first diode D1 having a first terminal and a second terminal, and matching capacitor Cm having a first terminal and a second terminal. Matching inductor Lm is connected at a first terminal with the first terminal of matching capacitor Cm. Matching capacitor Cm is connected at a first terminal with the first terminal of first inductor Ld. First inductor Ld is connected at a second terminal with the first terminal of first diode D1. First diode D1 is connected at a second terminal with the second terminal of matching capacitor Cm. Matching capacitor Cm is connected at a second terminal with a first input terminal of pre-amplifier 630. Matching inductor Lm is connected, at a second terminal, with a second input terminal of pre-amplifier 630. The first diode D1, matching capacitor Cm, and first inductor Ld isolate input to the preamplifier 630 from an induced high current or voltage in LC circuit 1110 when first diode D1 is forward biased. While in this example first inductor Ld, first diode D1, and matching capacitor Cm are illustrated on a connection path between the first terminal of matching inductor Lm and a first input terminal of preamplifier 630, in another embodiment, first inductor Ld, first diode D1, and matching capacitor Cm may be connected instead between the second terminal of matching inductor Lm and the second input terminal of preamplifier 630.

Figure 12:
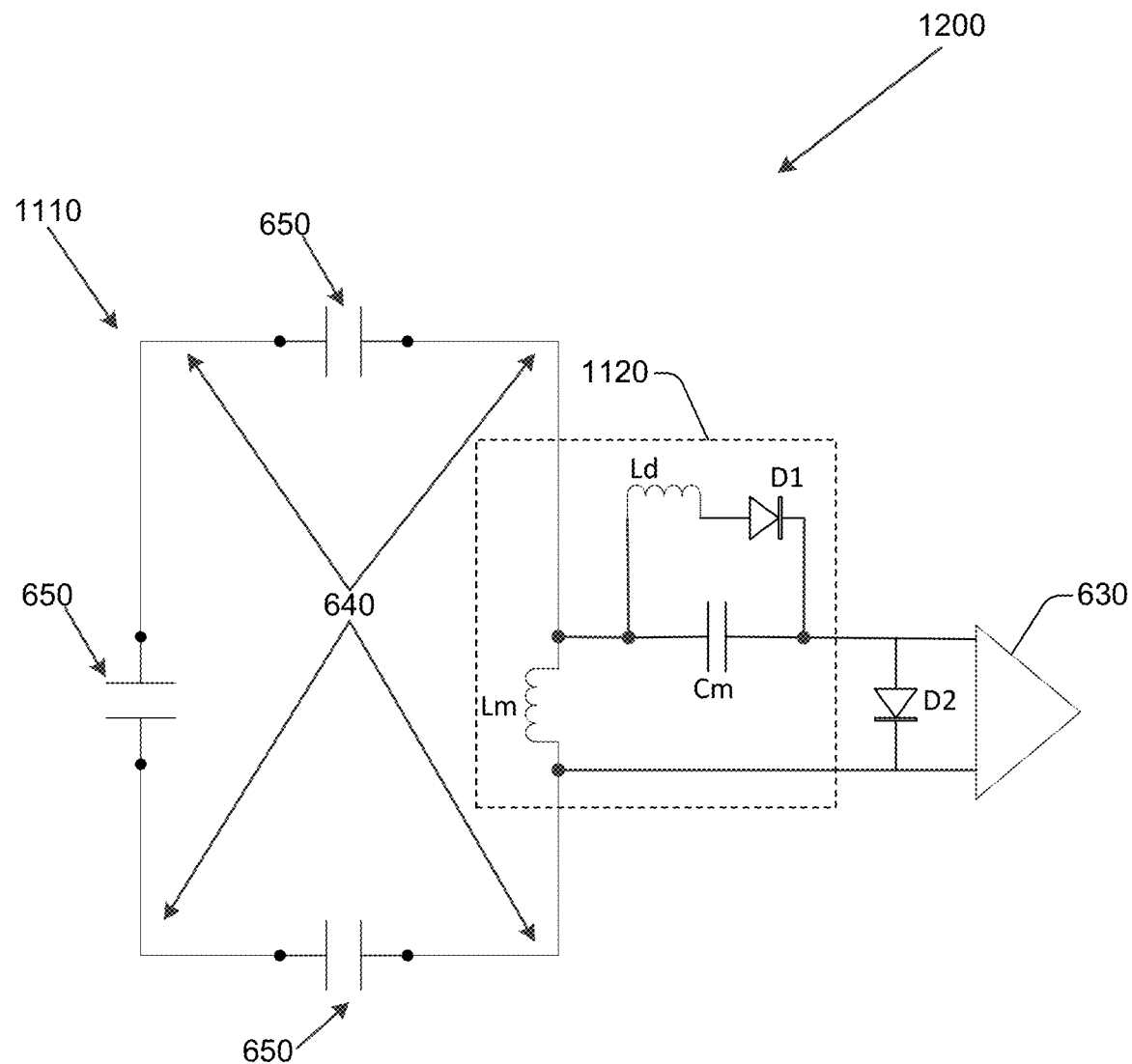
FIG. 12 illustrates an example single-layer MRI RF coil element.

FIG. 12 illustrates an MRI RF coil element 1200. MRI RF coil element 1200 is similar to MRI RF coil element 1100, but includes additional elements and details. MRI RF coil element 1200 may be part of a single-layer MRI RF coil array. The single-layer MRI RF coil array comprises at least one RF coil element 1200. MRI RF coil element 1200 includes shunt diode D2. Shunt diode D2 has a first terminal and second terminal. Shunt diode D2 is connected, at a first terminal, to a first input terminal of preamplifier 630. Shunt diode D2 is connected, at a second terminal, to a second input terminal of preamplifier 630. To further improve isolation between high current induced in LC coil 1110 and LNA preamplifier 630, shunt diode D2 provides additional shunt protection.

Embodiments described herein may include single-layer MRI RF coil arrays configured in shapes other than the cylindrical shape described above. For example, other shapes, including elliptical, rectangular, square, or other different shapes, may be used to build an Rx coil or single-layer MRI RF coil array for particular applications. For those shapes the concepts of the cylindrical case describe above are still applicable. Non-cylindrical shaped single-layer MRI RF coils may differ from cylindrical single-layer MRI RF coils in that the induced $B_1$ field of the other, non-cylindrical shapes is not as uniform as the induced $B_1$ field of the cylindrical case, but is still more than uniform enough for a Tx field in a clinical environment, including an iMRI procedure. The non-cylindrical shapes or cross sections discussed above are enclosed shapes or closed-shape configurations. Embodiments are not only applicable to an enclosed shape but may also be implemented as opened shapes, including MRI RF coil elements arranged on a single plane, on two parallel planes, on two planes that are within a threshold of parallel, or MRI RF coil elements arranged in an enclosed shape with a side not present, for example, a "C" shape or a "U" shape.

One embodiment of a single-layer MRI RF coil array that employs an opened shape includes a plurality of loops, saddles, or other MRI RF coil elements arranged on two parallel planes, or on non-parallel planes that are within a threshold tolerance of being parallel to each other, located at least a threshold distance apart, and that face each other directly. A threshold tolerance of being parallel may be, for example, a 1% tolerance, a 10% tolerance, or other, different tolerance. For example, a first point on a first MRI RF coil element may be located 20 cm from a corresponding first point on a facing, second MRI RF coil element, while a second point on the first MRI RF coil element may be located 22 cm from a corresponding second point on the second MRI RF coil element. In this embodiment, the size of the loops may be identical, or may be within a threshold margin of difference. For example, a first loop may describe an area of $x \text{cm}^2$, while a second loop may describe an area of $0.9x \text{ cm}^2$. In one embodiment, a plurality of different sized loops may be located on a first plane, while a second plurality of different sized loops may be located on a second, parallel plane, or on a second plane that is within a threshold tolerance of being parallel with the first plane.

Figure 13:
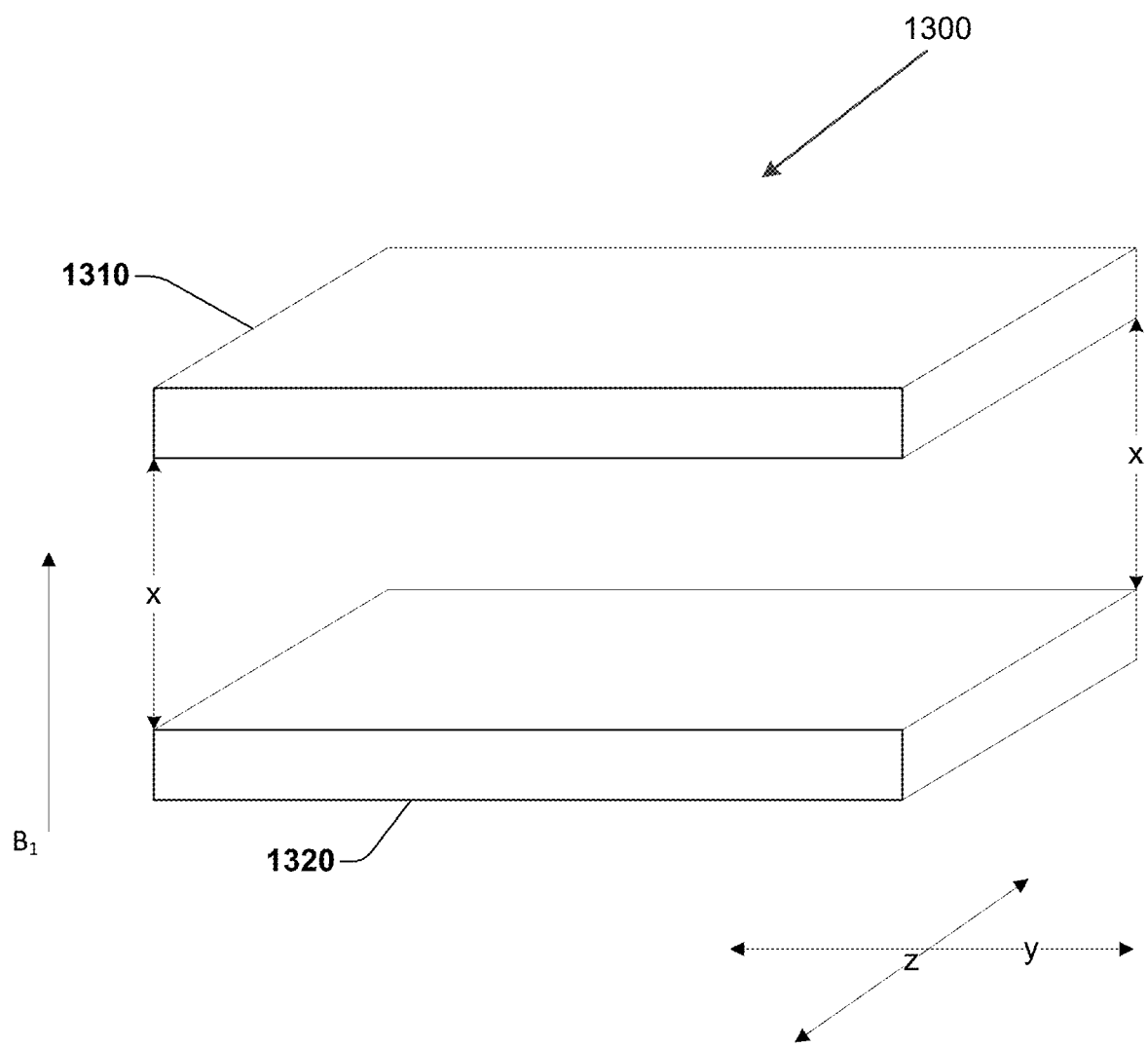
FIG. 13 illustrates an example open shape configuration single-layer MRI RF array.

FIG. 13 illustrates one embodiment of a single layer MRI RF coil array 1300 that includes at least two RF coil elements. While in this embodiment, only two RF coil loops are illustrated, in another embodiment, other, different numbers of RF coil loops may be employed. The at least two RF coil elements includes a first RF coil element 1310 and a second RF coil element 1320. First RF coil element 1310 and second RF coil element 1320 may include a single layer MRI RF coil element, including MRI RF coil element 600, 800, 900, 1000, 1100, 1200, or 1500, or other single-layer MRI RF coil elements described herein. First RF coil element 1310 is arranged on a first plane, while second RF coil element 1320 is arranged on a second, different plane parallel to the first plane. FIG. 13 illustrates an example open shape configuration. The first plane and the second plane may be parallel to each other, and are located at least a threshold distance from each other. The threshold distance is a distance greater than zero. The threshold distance may be a function of a volume to be imaged, for example, the size or shape of a human knee, wrist, or head. In this example, the at least a threshold distance is indicated by "x" in FIG. 13. The first plane and the second plane may, in another embodiment, be within threshold of parallel from each other. The first RF coil element 1310 and the second RF coil element 1320 may be offset laterally from each other a distance greater than zero, or may be directly aligned. For example, the first RF coil element 1310 and second RF coil element 1320 may be located 30 cm from each other in the x axis, and laterally offset 3 cm in the y axis or z axis. In other embodiments, other offsets may be employed.

First RF coil element 1310 and second RF coil element 1320 inductively couple to each other since they face each other. If both first RF coil element 1310 and second RF coil element 1320 are tuned independently to the same frequency without the presence of the other coil, their resonant frequency will split into two frequencies: a lower frequency and a higher frequency. The lower frequency is for the current of both RF coil element 1310 and RF coil element 1320 flowing in the same direction. The higher frequency is for the current of both RF coil element 1310 and RF coil element 1320 flowing in opposite directions. The frequencies may be written as $$f = \frac{1}{2\pi\sqrt{(L \pm M)C}},$$

where L is the inductance of the coil, C is the capacitance, and M is the mutual inductance between RF coil element 1310 and RF coil element 1320.

When both first RF coil element 1310 and second RF coil element 1320 are placed inside a WBC and the WBC generates a circular polarized (CP) uniform or a uniform $B_1$ field perpendicular to the planes of the coils, then the current induced in one of first RF coil element 1310 or second RF coil element 1320 by the WBC directly may be expressed as $$i_{1\_WBC} = \frac{\omega_0 A * B_1}{R} \quad \text{(Eq. 15)}$$

where A is the area of the loop, $B_1$ is the magnitude of WBC field, and R is the coil loss. In an example embodiment in which first RF coil element 1310 or second RF coil element 1320 includes RF coil element 600, 800, 900, 1000, 1100, 1200, or 1500, then the area A of the loop corresponds to the area of LC coil 610 or LC coil 1110. Here, R is the only term in the denominator of Eq. 15 because $$j\omega_0 L - j\frac{1}{\omega_0 C} = 0$$

at the resonant frequency $\omega_0$. The same current is also true for the other coil. For clarity, herein only the $B_1$ field perpendicular to the first plane and second plane is described. However, a $B_1$ field that is not perpendicular to the first plane and second plane may be described similarly. This is shown in equation 16 below.

$$i_{2\_WBC} = \frac{\omega_0 A * B_1}{R} \quad \text{(Eq. 16)}$$

Recall that both currents are flowing in the same direction. Because there is mutual inductance between first RF coil element 1310 and second RF coil element 1320, the final current $i_1$ of the first RF coil element 1310 includes the additional current caused by mutual inductance coupling. The final currents $i_1$ and $i_2$ can be written as:

$$i_1 = \frac{\omega_0 A * B_1}{R} - \frac{M \frac{d(i_{2\_WBC})}{dt}}{R} = \frac{\omega_0 A * B_1}{R} - M\frac{j(\omega_0^2 A * B_1)}{R^2} \quad \text{(Eq. 17)}$$

$$i_2 = \frac{\omega_0 A * B_1}{R} - \frac{M\frac{d(i_{1\ WBC})}{dt}}{R} = \frac{\omega_0 A * B_1}{R} - M\frac{j(\omega_0^2 A * B_1)}{R^2} \quad \text{(Eq. 18)}$$

Both $i_1$ and $i_2$ flow in the same direction and have the same current magnitude. In this example, the coupling or mutual inductance between the first loop or first RF coil element 1310 and the second loop or second RF coil element 1320 causes a Tx efficiency loss. Thus, the sign before M in equation 17 and equation 18 is "−", (i.e., negative sign). This embodiment thus may function as the equivalent of a two-turn solenoid or a saddle coil which generates a transmitting field that has a uniformity suitable for clinical use, including iMRI procedures. In another embodiment, other, different configurations of coils may be employed.

In one embodiment of single-layer MRI RF coil array 1300, a member of the at least two RF coil elements (e.g. first RF coil element 1310, second RF coil element 1320) includes an LC coil, a matching and Tx/Rx switch circuit, and a preamplifier. In this embodiment, the LC coil includes at least one inductor and at least one capacitor. The at least one inductor and the at least one capacitor resonate at a first frequency. The LC coil is connected with the matching and transmit Tx/Rx switch circuit. The matching and transmit Tx/Rx switch circuit is connected to the preamplifier. The matching and Tx/Rx switch circuit, when operating in Tx mode, electrically isolates the LC coil from the preamplifier upon the LC coil resonating with a primary coil at the first frequency. The LC coil, upon resonating with the primary coil at the first frequency, generates a local amplified Tx field based on an induced current in the LC coil. A magnitude of the induced current or a phase of the induced current is independently adjustable. For example, the magnitude or phase of the induced current may be variable over a range of magnitudes or phases respectively, by varying the coil loss resistance of the primary coil, the coil loss resistance of first RF coil element 1310 or second RF coil element 1320, or the difference between the working frequency of the primary coil and the resonant frequency of first RF coil element 1310 or second RF coil element 1320. The matching and Tx/Rx switch circuit, when operating in Rx mode, electrically connects the LC coil with the preamplifier. In one embodiment, the matching and Tx/Rx switch circuit is a capacitive matching and Tx/Rx switch circuit. In another embodiment, the matching and Tx/Rx switch circuit is an inductive matching and Tx/Rx switch circuit. In one embodiment, the LC coil includes a shunt PIN diode or protection PIN diode that provides further shunt protection to the preamplifier.

Figure 14:
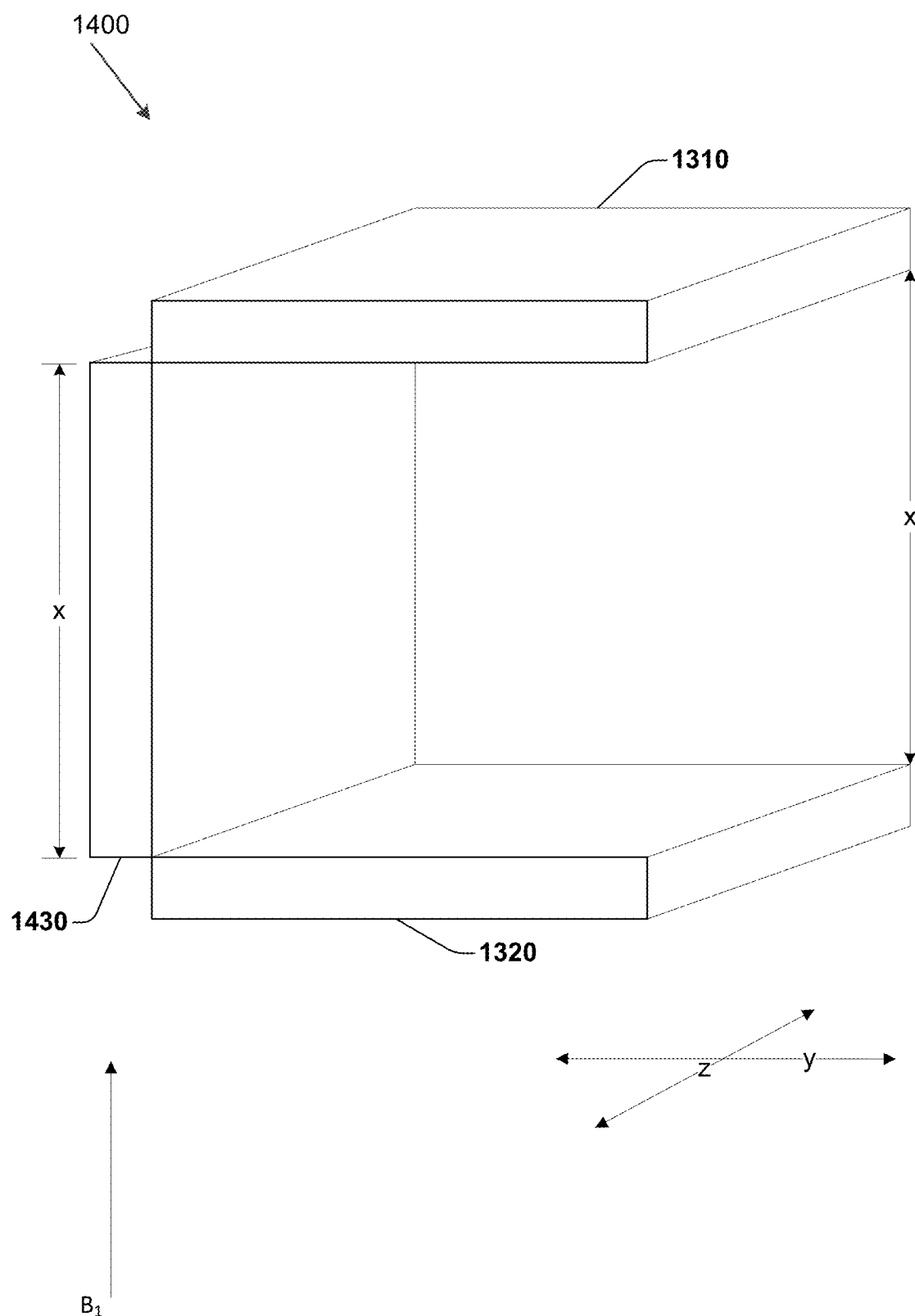
FIG. 14 illustrates an example open shape configuration single-layer MRI RF array.

FIG. 14 illustrates a single-layer MRI RF coil array 1400 that is similar to single-layer MRI RF coil array 1300 but that includes additional details and elements. Single-layer MRI RF coil array 1400 includes first RF coil element 1310, second RF coil element 1320, and also includes a third RF coil element 1430. FIG. 14 illustrates first RF coil element 1310, second RF coil element 1320, and third RF coil element 1430 disposed in an open shape configuration. In this embodiment, the RF coil elements 1310, 1320, and 1430 of MRI RF coil array 1400 are arranged approximately in the shape of a "C" or "U". First loop or RF coil element 1310 is arranged on a first plane, while second loop or RF coil element 1320 is arranged on a second, different plane. The first plane and the second plane may be parallel or slightly non-parallel to each other, and are located at least a threshold distance from each other. The threshold distance is a non-zero distance greater than zero. In this example, the at least a threshold distance is indicated by "x" in FIG. 14. In one embodiment, third RF coil element 1430 is arranged on a third plane that is perpendicular to the first plane and the second plane. In another embodiment, third RF coil element 1430 is arranged on a third plane that is within a threshold degree of parallel with the first plane or the second plane. For example, in one embodiment configured for a first anatomy to be imaged, the third RF coil element 1430 is arranged on a third plane that is perpendicular with the first plane and the second plane. In another embodiment configured for a second, different anatomy, the third RF coil element 1430 is arranged on a third plane that is not perpendicular with the first plane and the second plane. In one embodiment, an angle formed by the intersection of the third plane with the first plane or the second plane is user adjustable.

In one embodiment, third RF coil element 1430 is offset from the first RF coil element 1310 or the second RF coil element 1320 a non-zero amount along a y axis or a z axis. For example, the first RF coil element 1310 and second RF coil element 1320 may be located 30 cm from each other in the x axis, and laterally offset 3 cm in the y axis. The third RF coil element 1430 may be laterally offset 2 cm in the z axis from the first RF coil element 1310 and the second RF coil element 1320. In other embodiments, other offsets may be employed.

Third RF coil element 1430, like first RF coil element 1310 and second RF coil element 1320, may include an MRI RF coil element described herein, including MRI RF coil elements 600, 800, 900, 1000, 1100, 1200, or 1500. While three RF coil elements are illustrated, in another embodiment, other, different numbers of RF coil elements may be employed.

In one embodiment of single-layer MRI RF array coil 1400, a member of the at least three RF coil elements (e.g. first RF coil element 1310, second RF coil element 1320, third RF coil element 1430) includes an LC coil, a matching and transmit (Tx)/receive (Rx) switch circuit, and a preamplifier. In this embodiment, the LC coil includes at least one inductor and at least one capacitor. The at least one inductor and the at least one capacitor resonate at a first frequency. The matching and Tx/Rx switch circuit, when operating in Tx mode, electrically isolates the LC coil from the preamplifier upon the LC coil resonating with a primary coil at the first frequency. The LC coil, upon resonating with the primary coil at the first frequency, generates a local amplified Tx field based on an induced current in the LC coil. A magnitude of the induced current or a phase of the induced current is independently adjustable. The matching and Tx/Rx switch circuit, when operating in Rx mode, electrically connects the LC coil with the preamplifier. In one embodiment, the matching and Tx/Rx switch circuit is a capacitive matching and Tx/Rx switch circuit. In another embodiment, the matching and Tx/Rx switch circuit is an inductive matching and Tx/Rx switch circuit. In one embodiment, the LC coil includes a shunt PIN diode or protection PIN diode that provides further shunt protection to the preamplifier.

Embodiments described herein may also be described using a mode approach. For example, two identical coils facing each other may both resonate at the same frequency if the other coil does not exist. Due to mutual inductance the two coils create two intrinsic resonant modes. The first mode is the lower frequency mode which is called saddle mode or corotation mode, where both coils' currents flow in the same direction. The other mode has a higher frequency and is called anti-saddle mode or counter-rotation mode in which the currents of the coils flow in opposite directions. If a uniform external field or a circular polarized uniform external field is applied to the coils, only the saddle mode configuration will have induced voltage because its net flux is non-zero while the anti-saddle mode's net flux is zero. As a result two identical coils, or coils having sufficient similarity, facing each other will generate an amplified B1 field by the local saddle mode which has a level of uniformity suitable for clinical use, including iMRI use. The external uniform field serves as a selector for modes. The larger the net magnetic flux the mode has, the more energy from the external field is coupled.

This discussion can also be extended to embodiments that employ a plurality of MRI RF coil elements. For example, in an embodiment with N coil elements in which some or all of the N coil elements' isolations may not be good (i.e., the isolation may not be within a threshold tolerance), the N coil elements will couple to each other and create M Eigen-resonant modes in which a mode is a sum of some or all coil elements with different weighting coefficients and phases, where N and M are integers. In this embodiment, a mode is excited proportionally by the net magnetic flux of each mode from the WBC. The most uniform mode among all modes has the largest net magnetic flux from the WBC. For example, a two-element embodiment will be more uniform among modes. Therefore, the most uniform mode among the modes is the strongest mode excited by the WBC. If other less uniform modes' net magnetic fluxes from the WBC are not zero, they will be also excited but the induced fields from them are weaker than the most uniform mode, on average. The other less uniform modes make the final combined induced field more uniform than the induced field from the most uniform mode only. Thus, the final combined induced field is sufficiently uniform for use in clinical MRI applications, including iMRI procedures.

In summary, a plurality of single-layer MRI RF coils or MRI RF coil elements configured as a single-layer MRI RF coil array, resonating with a WBC coil in Tx mode will induce a local amplified Tx field. A coil array element may have the magnitude and phase of an induced current adjusted independently of another, different coil array element. The local amplified Tx field has a threshold level of uniformity and the single-layer MRI RF coil array is used as a transmitter coil. This amplified Tx field improves the WBC power efficiency and reduces the SAR compared to conventional approaches because non-related anatomy areas will not experience a high Tx field from the WBC. Because the Tx field is adjustable via independent phase or magnitude control, the RF heating of an iMRI guidewire that is subjected to the Tx field may be minimized or controlled by varying the uniformity of the local amplified Tx field. In one embodiment, MRI RF array coils that connect to an MRI system can be connected through cables or may be connected wirelessly with no cables.

Embodiments described herein are configured such that the magnitude of the induced current or the phase of the induced current are variable over a range of magnitudes or phases respectively. Example embodiments adjust the magnitude and phase of the induced current $i_s$ of a coil in Tx mode such that the image quality is still acceptable for MRI or iMRI purposes. When a single-layer MRI RF coil array operates in Rx mode, it operates as a phased array receiving coil with a frequency tuned to the working frequency for optimum SNR. Embodiments described herein provide magnitude and phase adjustment for an RF coil operating in Tx mode. Different approaches to adjust a coil's magnitude and phase are now described herein.

Recall from equation 3 that the local inductively coupled coil current can be written as:

$$i_s = \frac{-j\omega M \varepsilon}{(R_p R_s + \omega^2 M^2)} \quad \text{(Eq. 3.1)}$$

where $i_s$ is the induced current of local RF coil, $R_p$ is the coil loss resistance of the WBC, $R_s$ is the coil loss resistance of the local RF coil, M is the mutual inductance between the WBC and the local RF coil and e is the driving voltage of the WBC. Eq. 3.1 immediately above assumes that both the WBC and the local RF coil resonate at the same working frequency. Because the local coil is smaller than the WBC, the magnetic field generated by $i_s$ is significantly larger than the magnetic field generated from the WBC. Therefore the Tx field is dominated by the local coil. The WBC is part of the iMRI system and its frequency is fixed at the nominal working frequency. Typically, the working frequency of the WBC cannot be changed, and typically, a WBC cannot be removed from an iMRI system in normal clinical practice.

Embodiments are configured to adjust the magnitude and phase of the induced $i_s$ of a coil (e.g., a loop, a coil array element) in a single-layer MRI RF coil array while operating in Tx mode, and facilitate ensuring that the coil Tx mode is a low heat mode and that the image quality is still acceptable for an iMRI procedure. Embodiments thus provide the equivalent to a pTx coil without requiring the use of an expensive pTx system. When a coil in a single-layer MRI RF coil array is operating in Rx mode, it operates as a phased array receiving coil where a coil's frequency is tuned to the working frequency for optimum SNR.

Figure 15:
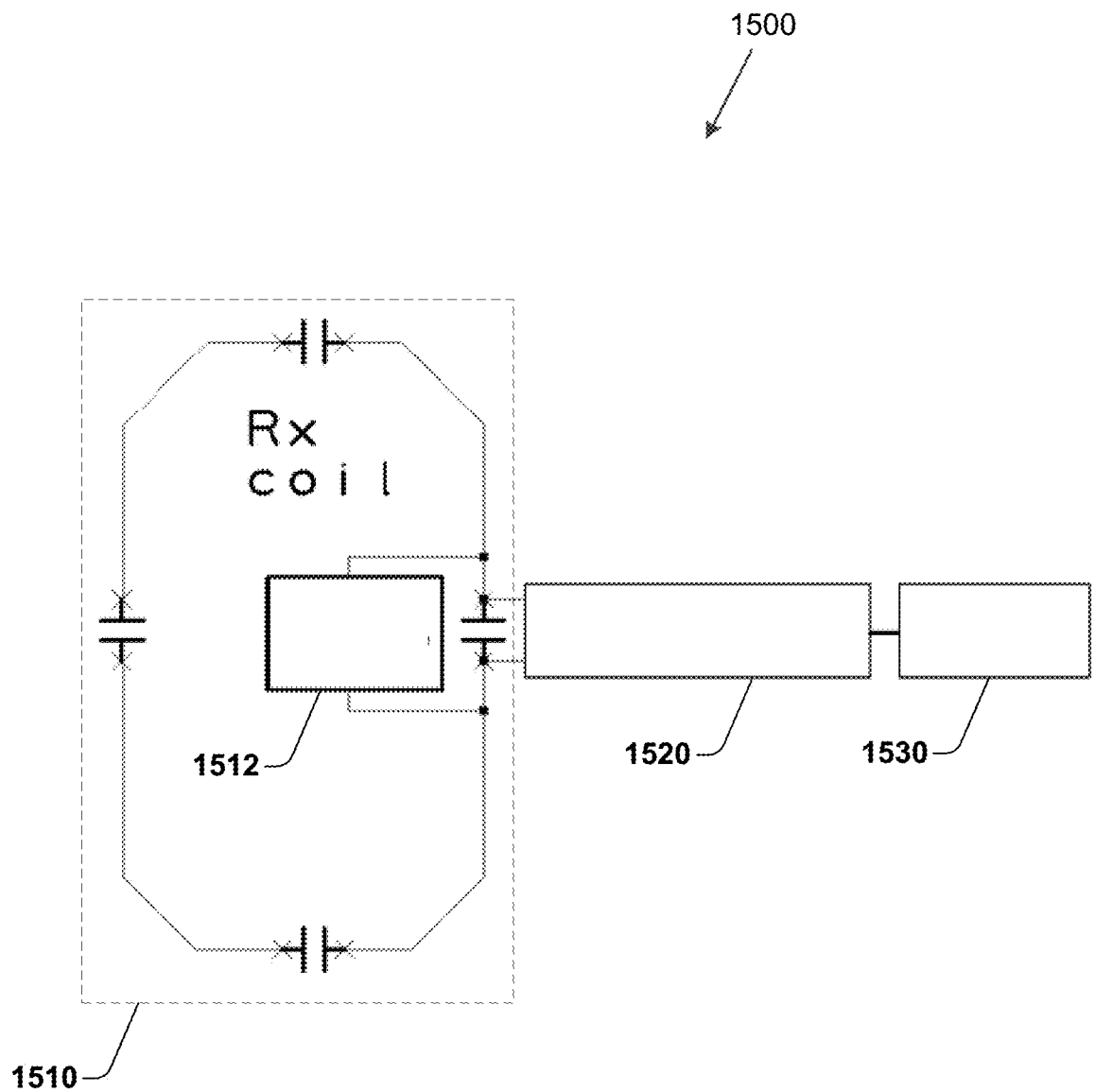
FIG. 15 illustrates an example single-layer MRI RF coil element.

FIG. 15 illustrates an example single-layer MRI RF coil array element 1500 configured to operate in a Tx mode and an Rx mode. Single-layer MRI RF coil array element 1500 is similar to RF coil element 600, 800, 900, 1000, 1100, or 1200, but includes additional elements and details. Single-layer MRI RF coil array element 1500 includes an LC coil 1510, a matching and Tx/Rx switch circuit 1520 operably connected to the LC coil 1510, and a preamplifier or other Rx electronics 1530 operably connected to the matching and Tx/Rx circuit 1520. LC coil 1510 further includes a magnitude/phase control component 1512 operably connected to LC coil 1510.

LC coil 1510 includes at least one inductor and at least one capacitor, where the at least one inductor and the at least one capacitor resonate at a first frequency. The first frequency may be, for example, the working frequency. In one embodiment, LC coil 1510 may be configured as LC coil 610 illustrated in FIG. 6, 8, 9, or 10. In another embodiment, LC coil 1510 may be configured as LC coil 1110 as illustrated in FIG. 11 or 12.

In one embodiment, LC coil 1510 includes at least one conductor. The at least one conductor may be a flexible co-axial cable. Thus, LC coil 1510 may be configured as a flexible LC coil, and single-layer MRI RF coil array element 1500 may be configured as a flexible single-layer MRI RF coil array element.

The matching and Tx/Rx switch circuit 1520, when operating in Tx mode, electrically isolates LC coil 1510 from preamplifier 1530 upon LC coil 1510 resonating with a primary coil (not illustrated). The primary coil has a working frequency.

In one embodiment, the matching and Tx/Rx switch circuit 1520 is a capacitive matching and Tx/Rx switch circuit. For example, matching and Tx/Rx switch circuit

1520 may be configured as matching and Tx/Rx switch circuit 820 illustrated in FIG. 8. In another embodiment, matching and Tx/Rx switch circuit 1520 may be configured as matching and Tx/Rx switch circuit 920 illustrated in FIG. 9. In another embodiment, matching and Tx/Rx switch circuit 1520 may be configured using other, different matching and Tx/Rx switch circuitry configurations.

LC coil 1510, upon resonating with the primary coil, generates a local amplified Tx field based on an induced current in LC coil 1510. The induced current is generated by inductive coupling between LC coil 1510 and the primary coil. A magnitude of the induced current or a phase of the induced current is independently adjustable. The magnitude of the induced current or the phase of the induced current is configured to be varied over a range of magnitudes or phases respectively.

The matching and Tx/Rx switch circuit 1520, when operating in Rx mode, electrically connects LC coil 1510 with preamplifier 1530.

The magnitude/phase control component 1512 is configured to adjust the magnitude of the induced current or the phase of the induced current. In one embodiment, the magnitude/phase control component 1512 is configured to, upon the single-layer MRI RF coil array element operating in Tx mode, adjust the magnitude of the induced current or the phase of the induced current by shifting the first frequency of the LC coil relative to the working frequency of the primary coil. For example, in one embodiment, magnitude/phase control component 1512 is configured to use a first approach to adjust a magnitude of the induced current or the phase of the induced current by shifting the MR coil's (e.g., LC coil 1510) resonant frequency from the working frequency of the WBC. Recall that the induced current $i_s$ may be expressed as:

$$i_s = \frac{-j\omega M\varepsilon}{\left(R_p R_s + \omega^2 M^2 + jR_p\left(\omega L_s - \frac{1}{\omega C_s}\right)\right)} \quad \text{(Eq. 4)}$$

where there is an additional term $$jR_p\left(\omega L_s - \frac{1}{\omega C_s}\right)$$

in the denominator.

If the coil frequency is same as the working frequency, this additional term has a value of zero. Example embodiments adjust this new term by changing the frequency to either higher than the working frequency or lower than the working frequency. This facilitates adjusting the magnitude and phase of the induced current $i_s$ simultaneously. If the magnitude and phase of $i_s$ are changed, the magnitude and phase of the induced field is also changed. Thus we have a coil that is a pTx-equivalent coil. Eq. 4 changes magnitude and phase simultaneously. In some situations, it may be desirable to have additional freedom to control magnitude and phase independently.

In another embodiment, magnitude/phase control component 1512 is configured to use a second approach to adjust a coil's magnitude and phase by independently adding additional coil loss (i.e., resistance) when operating in Tx mode. For example, in one embodiment, the magnitude/phase control component 1512 is configured to, upon the single-layer MRI RF coil array element 1500 operating in Tx mode, adjust the magnitude of the induced current or the phase of the induced current by adding coil loss to the LC coil 1510. In this embodiment, the magnitude/phase control component 1512 comprises a resistor and a PIN diode connected in parallel with the at least one capacitor, where the single-layer MRI RF coil array element 1500 operates in Tx mode upon the injection of a DC bias into the PIN diode, where the DC bias forward biases the PIN diode.

Figure 16:
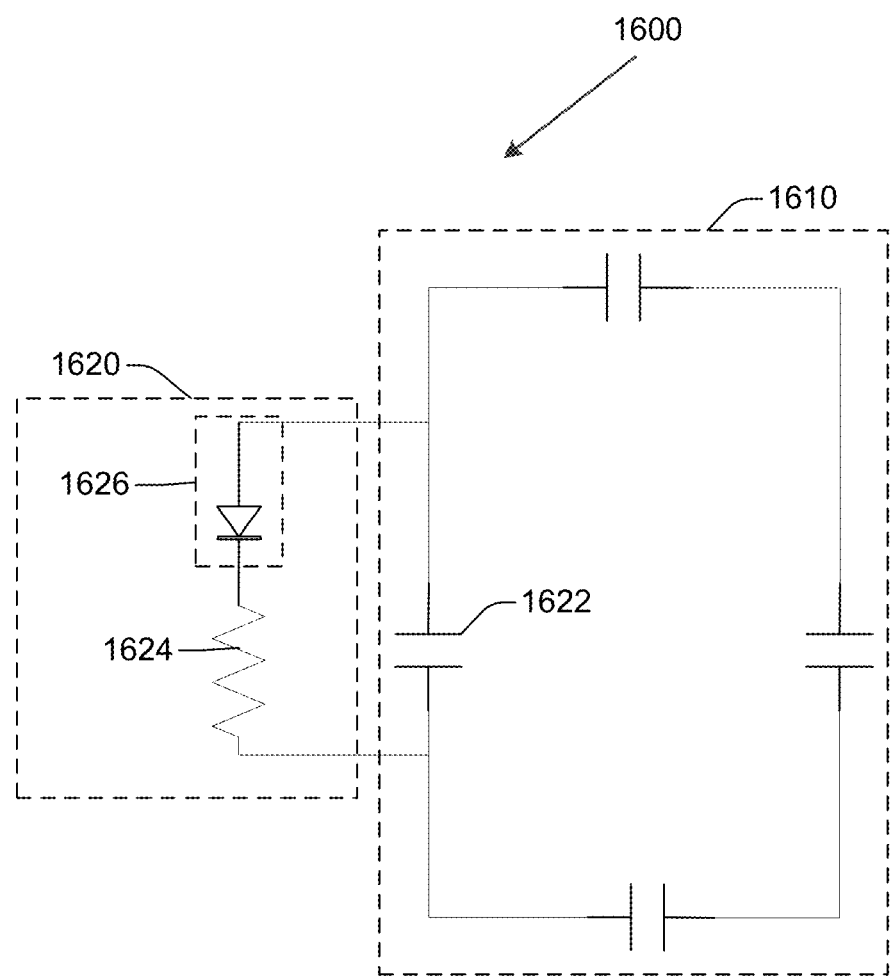
FIG. 16 illustrates an example single-layer MRI RF coil element.

This second approach includes increasing $R_s$ when operating in Tx mode. Increasing $R_s$ reduces the magnitude alone if the coil's resonant frequency is the same as the working frequency. Increasing $R_s$ reduces both magnitude and phase if the coil's resonant frequency and the working frequency are different. One example implementation of this second approach is illustrated in FIG. 16, which includes adding coil loss. In this embodiment, the single-layer MRI RF coil array element 1600 includes a magnitude/phase control component 1620, and LC coil 1610 that includes one or more breaking point capacitors 1622. A resistor 1624 is added in parallel to the capacitor 1622 through a PIN diode 1626. Matching and Rx/Tx 1520 and 1530 are not illustrated for clarity. The breaking point can also be a feeding point, i.e., a matching capacitor. In Tx mode the PIN diode 1626 is shorted and the resistor 1624 is in parallel with capacitor 1622, which causes $R_s$ to increase. The value of $R_s$ may be chosen to meet particular magnitude and phase requirements for different heating modes, including low heating modes. The resistor 1624 is configured to be powerful enough to take a high current in Tx mode. For example, resistors having resistance within the kilo-Ohms range may be employed to reduce current magnitude significantly. The smaller the resistor value, the lesser the current magnitude, and the lower the coil Q in Tx mode. In Rx mode the PIN diode 1626 is open, and the resistor 1624 is therefore not part of the coil resistance. This still results in a high Q receiving coil.

In another embodiment, the magnitude/phase control component 1512 is configured to, upon the single-layer MRI RF coil array element 1500 operating in Tx mode, adjust the magnitude of the induced current or the phase of the induced current by decreasing the induced current. In this embodiment, the magnitude/phase control component 1512 is configured to decrease the induced current by operating as a parallel resonant circuit when in Tx mode. In this embodiment, the magnitude/phase control component 1512 comprises an inductor and a PIN diode connected in parallel with a first member of the at least one capacitor, where the first member of the at least one capacitor has a higher capacitance than a second, different member of the at least one capacitor, where the single-layer MRI RF coil array element operates in Tx mode upon the injection of a DC bias into the PIN diode, where the DC bias forward biases the PIN diode. In one embodiment, the magnitude/phase control component 1512 introduces a blocking impedance of less than one-hundred Ohms to the LC coil when operating in Tx mode.

Figure 17:
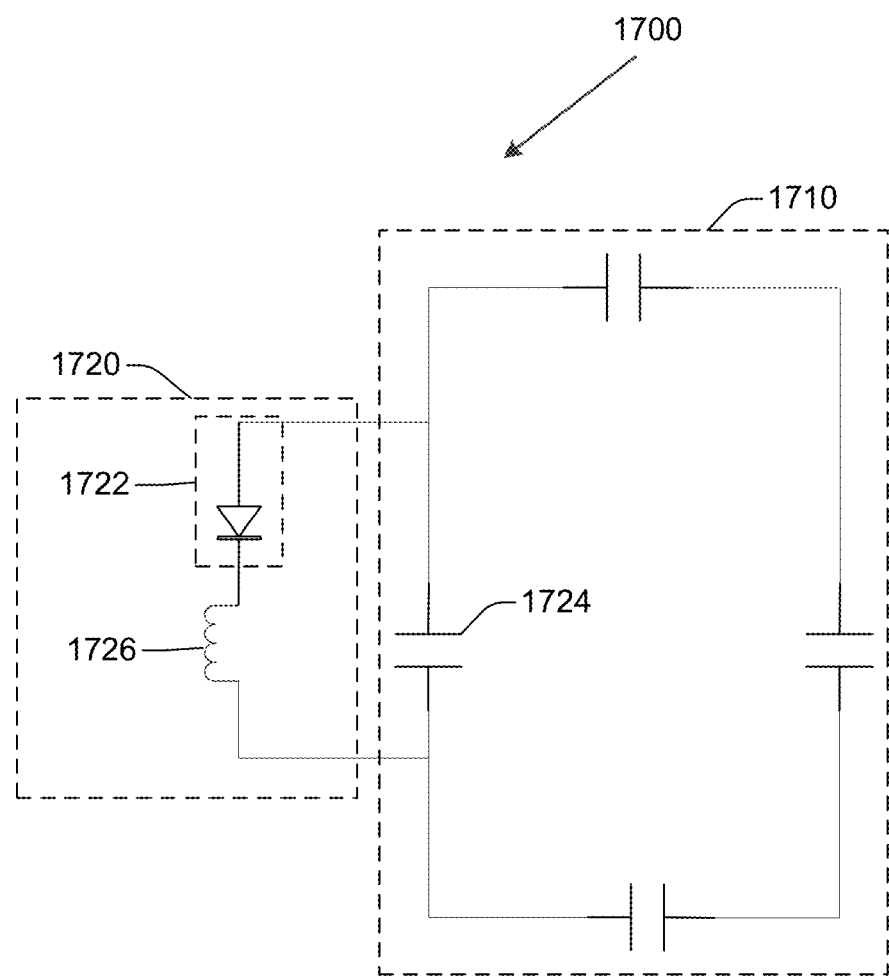
FIG. 17 illustrates an example single-layer MRI RF coil element.

For example, in one embodiment, magnitude/phase control component 1512 is configured to use a third approach that includes introducing a parallel resonant circuit in the coil when operating in Tx mode only. One example implementation of this third approach is illustrated in FIG. 17. FIG. 17 illustrates a single-layer MRI RF coil array element 1700 that includes LC coil 1710, and magnitude/phase control component 1720. Magnitude/phase control component 1720 is configured as an LC parallel resonant circuit. Magnitude/phase control component 1720 includes a PIN diode 1722 that controls magnitude/phase control component 1720 to minimize the induced current in a coil 1710 when operating in Tx mode. Typically, the blocking impedance of magnitude/phase control component 1720 when operating in Tx mode as an LC parallel resonant circuit is very large, e.g., several kOhm. This impedance almost completely eliminates the induced current in coil 1710. Example embodiments may still need to use the induced current. Thus, example embodiments may reduce current magnitude, but do not need to almost completely eliminate the current. Therefore example embodiments may employ a weak blocking impedance of several Ohms to tens of Ohms, instead of a strong blocking impedance of several kOhms. Example embodiments may use a capacitor 1724 having a large value of capacitance and inductor 1726 having a small value of inductance to resonate. Magnitude/phase control component 1720 may be installed anywhere in LC coil 1710 to reduce the induced current in Tx mode only by operating as a parallel resonant circuit. Recalling that $$i_s = \frac{-j\omega M\varepsilon}{(R_p R_s + \omega^2 M^2)}$$

and Eq. 4, example embodiments thus facilitate controlling current magnitude by changing the value of $R_s$. In Rx mode the PIN diode 1722 is open.

Figure 18:
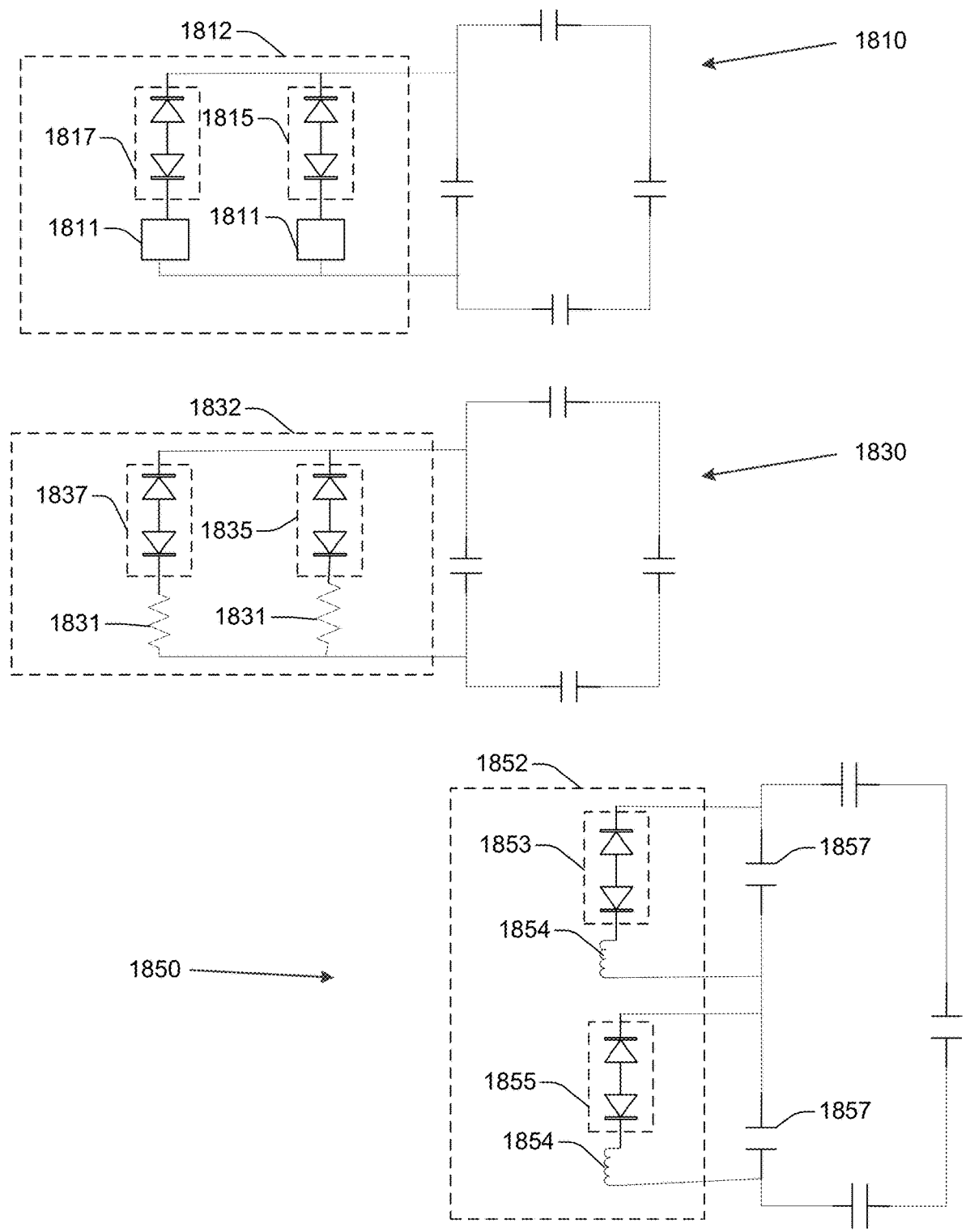
FIG. 18 illustrates example single-layer MRI RF coil elements.

The three approaches to adjust a coil's magnitude and phase described above may be employed together to create a mode selection approach for different induced current magnitudes and phases for the same coil in Tx mode. This approach is shown in FIG. 18. FIG. 18 illustrates single-layer MRI RF coil array elements 1810, 1830, and 1850. For clarity of illustration, FIG. 18 does not include matching and Tx/Rx switch circuitry or a preamplifier or other Rx electronics. FIG. 18 illustrates magnitude/phase control components 1812, 1832, and 1852 which are configured to provide two-mode switching. Mode switching is conducted by applying a bias to PIN diode pairs 1815 and 1817, 1835 and 1837, or 1853 and 1855. Each of PIN diode pairs 1815 and 1817, 1835 and 1837, or 1853 and 1855 includes a pair of back-to-back PIN diodes. In other embodiments, three or more modes switching may be implemented by adding more back to back diodes into the path. The back to back diodes in PIN diode pairs 1815 and 1817, 1835 and 1837, or 1853 and 1855 have reverse polarization from each other. The PIN diodes' breakdown voltage may be greater than the induced voltage across the capacitor 1811, 1834, or 1857 respectively when operating in Tx mode. In Tx mode only one pair of diodes (e.g., either PIN diode pair 1815 or PIN diode pair 1817) will be ON (short). For example, PIN diode pair 1815 can be ON(short) and PIN diode pair 1817 can be OFF (open) or vice versa in Tx mode. The PIN diode pair 1815 pair path and the PIN diode pair 1817 pair path will have different induced magnitude and phase. These different magnitudes and phases may be used for different purposes depending on particular clinical scanning requirements. If one of the PIN diode pairs is not ON while the other one is ON, the breakdown voltage that is greater than the induced voltage across the capacitor will ensure the not-ON PIN diode pair path is not part of the coil and the pair of PIN diodes survives the currents generated when operating in Tx mode. The approach may be extended to more than two modes switching, such as three modes, four modes, or more modes.

Magnitude/phase control component 1812 is configured to provide control of two different switchable magnitudes and phases by frequency shifting using reactance. Reactance components 1811 may include a capacitor or an inductor.

Magnitude/phase control component 1832 is configured to provide control of two different switchable magnitudes and phases using coil losses generated with the resistor-based approach described with respect to FIG. 16. Thus, magnitude/phase control component 1832 is similar to magnitude/phase control component 1812, but includes resistors 1831 instead of reactance components 1811.

Magnitude/phase control component 1852 is configured to provide control of two different switchable magnitudes and phases control using coil loss produced by the LC parallel resonance approach described with respect to FIG. 17. Magnitude/phase control component 1852 includes inductors 1854 configured to operate similarly to inductor 1726.

Example embodiments thus provide circuits, components, means, or techniques to facilitate independent magnitude and phase control for an MRI RF coil by solving the magnitude and phase equation with the controllable variables as described above. Furthermore, example embodiments facilitate choosing more than one different magnitude and phase combinations, i.e., more than one different Tx field pattern for different scanning or different heat mode imaging requirements. In embodiments described herein, these approaches create Tx fields in Tx mode. In Rx mode, coils described herein operate as a phased array coil at the nominal working frequency.

Figure 19:
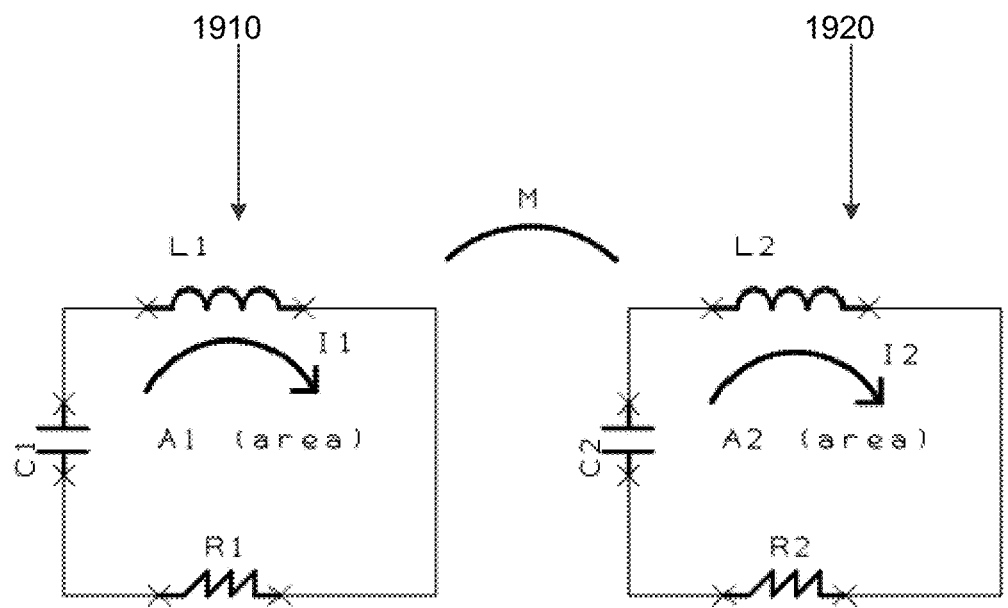
FIG. 19 illustrates inductively coupled resonant RF coils.

In addition to an induced current from a WBC field, an MRI RF coil array element as described herein may experience induced current from other MRI RF coil array elements due to non-trivial mutual inductance among the MRF RF coil array element and the other MRI RF coil array elements. FIG. 19 demonstrates this induced current. Two MRI RF coil array elements 1910 and 1920 exposed in a uniform $B_1$ field of a WBC are shown in FIG. 19. The two coil elements 1910 and 1920 have areas A1 and A2 respectively. The uniform $B_1$ field is applied perpendicularly to areas A1 and A2. The two coil elements 1910 and 1920 have non-trivial mutual inductance between them. The self inductances L1 and L2, capacitances C1 and C2, coil losses R1 and R2, current flow I1 and I2, and projected areas A1 and A2 for coil elements 1910 and 1920 respectively are illustrated as shown in FIG. 19.

From FIG. 19, equations 19 and 20 may be defined:

$$j\omega_0 B_1 A_1 = j\omega_0 L_1 I_1 + \frac{1}{j\omega_0 C_1} I_1 + R_1 I_1 + j\omega_0 M I_2 \quad \text{Eq. 19}$$

$$j\omega_0 B_1 A_2 = j\omega_0 L_2 I_2 + \frac{1}{j\omega_0 C_2} I_2 + R_2 I_2 + j\omega_0 M I_1 \quad \text{Eq. 20}$$

In one embodiment, assuming that both coil 1910 and coil 1920 also resonate at $\omega_0$ in Tx mode, then Eq. 19(3) and 20(4) can be simplified as below:

$$j\omega_0 B_1 A_1 = R_1 I_1 + j\omega_0 M I_2 \quad \text{Eq. 21}$$

$$j\omega_0 B_1 A_2 = R_2 I_2 + j\omega_0 M I_1 \quad \text{Eq. 22}$$

Solving equations 21 and 22 results in:

$$I_1 = \frac{j\omega_0 B_1 A_1 - j\omega_0 B_1 A_2 \frac{j\omega_0 M}{R_2}}{\frac{(\omega_0 M)^2}{R_2} + R_1} \quad \text{Eq. 23}$$

-continued $$I_2 = \frac{j\omega_0 B_1 A_2 - j\omega_0 B_1 A_1 \frac{j\omega_0 M}{R_1}}{\frac{(\omega_0 M)^2}{R_1} + R_2} \quad \text{Eq. 24}$$

If mutual inductance is not trivial, i.e., $\omega_0 M \gg R_1$ and $R_2$, and if the values $A_1$ and $A_2$ are not significantly different, then Eq. 23 and 24 can be simplified as:

$$I_1 \cong \frac{-j\omega_0 B_1 A_2 \frac{j\omega_0 M}{R_2}}{\frac{(\omega_0 M)^2}{R_2} + R_1} \quad \text{Eq. 25}$$

$$I_2 \cong \frac{-j\omega_0 B_1 A_1 \frac{j\omega_0 M}{R_1}}{\frac{(\omega_0 M)^2}{R_1} + R_2} \quad \text{Eq. 26}$$

Thus, $I_1$ is determined by the WBC induced voltage in coil 1920, that is, by its neighbor coil 1910 instead of coil 1920 itself, and vice versa. Consequently, the local mutual inductance coupled modes among local array coils are dominant if the mutual inductances are not trivial. Therefore, the final induced field of the array coils (e.g., 1910 and 1920) from the WBC is the sum of the WBC induced fields from coils with trivial mutual inductance from other elements and the local coupled modes among the coils having non-trivial mutual inductances. The local coupled modes may have multiple different frequencies and different Tx field patterns. Depending on the application in which coil 1910 and coil 1920 are being employed, (e.g, for a first anatomy, for a second, different anatomy, for an iMRI procedure) the correct local coupled mode or modes must be adjusted in such a way that its or their frequencies must be same as the working frequency $\omega_0$.

Figure 20:
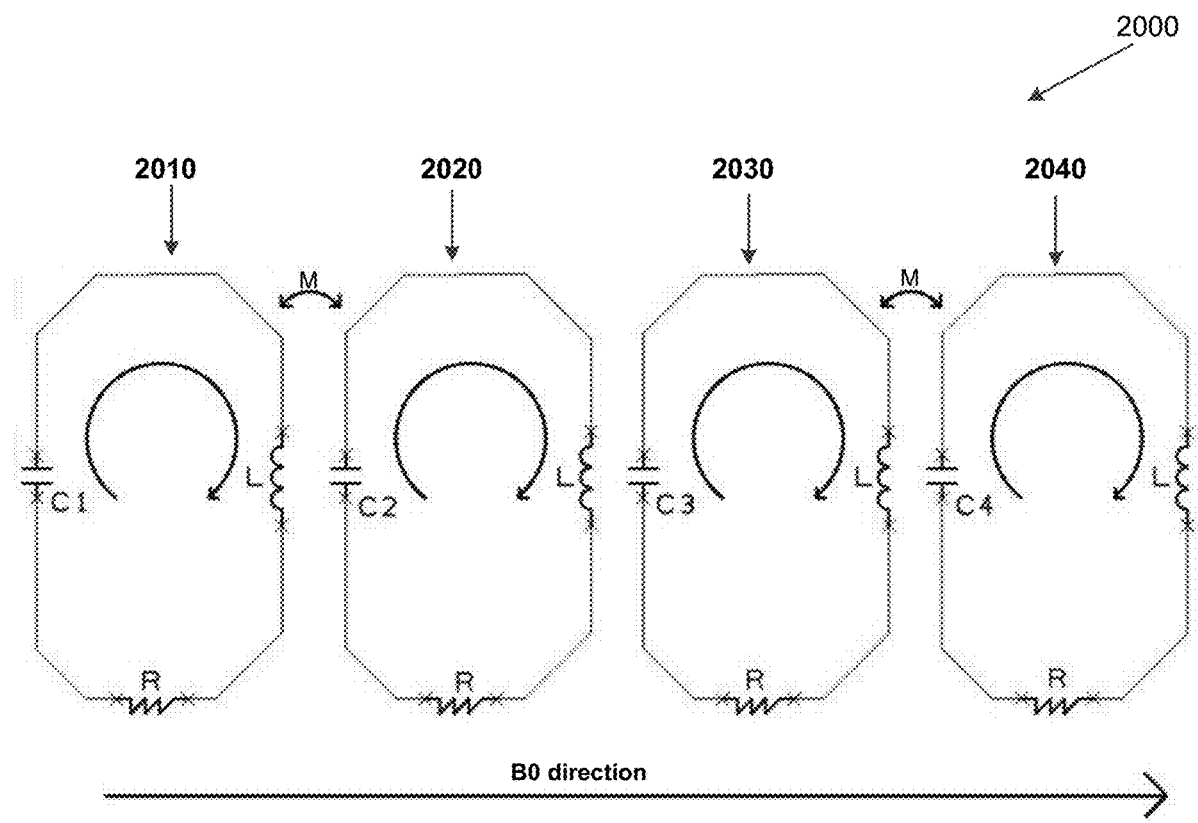
FIG. 20 illustrates an example single-layer MRI RF coil array.

FIG. 20 illustrates an example embodiment of a four-channel single-layer MRI RF coil array 2000 configured to operate in a low heat mode. In FIG. 20, single-layer MRI RF coil array 2000 is illustrated operating in Tx mode. MRI RF coil array 2000 includes four single-layer MRI RF coil array elements 2010, 2020, 2030, and 2040. In this example, the magnitudes and phases of induced current in single-layer MRI RF coil array elements 2010, 2020, 2030, and 2040 are configured in a low heat mode. Single-layer MRI RF coil array elements 2010, 2020, 2030, and 2040 may be, for example, embodiments of single-layer MRI RF coil array elements 1500 described herein. The four single-layer MRI RF coil array elements 2010, 2020, 2030, and 2040 are arranged in one row and on the same plane. In this example, the row is oriented in the $B_0$ direction as illustrated. In another embodiment, other different numbers of single-layer MRI RF coil array elements may be arranged in other configurations of rows.

In this example, single-layer MRI RF coil array elements 2010 and 2040 each have areas A1 having the same, first, value. Single-layer MRI RF coil array elements 2020 and 2030 each have areas A2 having the same, second value, where area A1 does not equal area A2. In embodiments described herein, the area A1 must exceed a threshold level of difference from A2, e.g., be at least 20% different. For clarity of calculation, in this example, all single-layer MRI RF coil array elements 2010, 2020, 2030, and 2040 have the same coil inductance, defined as L. This coil inductance can be achieved by putting an extra solenoid inductor into a smaller area coil (e.g. single-layer MRI RF coil array elements 2020 and 2030) to boost their inductance.

In this example, for clarity of calculation, all single-layer MRI RF coil array elements 2010, 2020, 2030, and 2040 have the same resistance R, which can be achieved by adding a small resistor into the single-layer MRI RF coil array elements 2010, 2020, 2030, and 2040 to make their resistances R equal. Each of the single-layer MRI RF coil array elements' 2010, 2020, 2030, and 2040 resonances is adjusted by adjusting its capacitance C, illustrated as C1, C2, C3 and C4. In this example, single-layer MRI RF coil array elements 2010, 2020, 2030, and 2040 have the same current magnitude but different phases, such as 180 degrees, 0 degrees, 0 degrees, and 180 degrees per the definition of current flow direction. While in a conventional iMRI system, the phases of the induced current in MRI RF coil array elements may be controlled using complex and expensive pTx techniques to drive the MRI RF coil array elements, embodiments described herein control the magnitude and phase independently using, for example, example single-layer MRI RF coil array elements configured with exemplary magnitude/phase control components or circuitry, without requiring pTx systems.

Single-layer MRI RF coil array elements 2010 and 2020 experience non-trivial mutual inductance by choosing an overlap between single-layer MRI RF coil array elements 2010 and 2020 that is less than a perfect overlap, i.e., an under-overlap. Single-layer MRI RF coil array elements 2030 and 2040 are similarly arranged (i.e., with an under-overlap). Mutual inductance between coil array elements may be considered as trivial when they are either direct neighbors, in which situation the mutual inductance can be minimized using a particular overlap, such as between single-layer MRI RF coil array elements 2020 and 2030, or when they are far enough away from each other that the mutual inductance is small, such as between single-layer MRI RF coil array elements 2010 and 2030, between single-layer MRI RF coil array elements 2010 and 2030, and between single-layer MRI RF coil array elements 2020 and 2040.

Based on the example illustrated in FIG. 20, the following equations for single-layer MRI RF coil array elements 2010 and 2030, which are similar to Eq. 19 and 20, may be derived:

$$j\omega_0 B_1 A_1 = j\omega_0 L I_1 + \frac{1}{j\omega_0 C_1} I_1 + R I_1 - j\omega_0 M I_2 \quad \text{Eq. 27}$$

$$j\omega_0 B_1 A_2 = j\omega_0 L I_2 + \frac{1}{j\omega_0 C_2} I_2 + R I_2 - j\omega_0 M I_1 \quad \text{Eq. 28}$$

where $B_1$ is the magnetic field from the WBC.

In this example, the signs before $j\omega_0 M$ in Eq. 27 and Eq. 28 are negative because single-layer MRI RF coil array element 2010's field will decrease single-layer MRI RF coil array element 2020's field per the current direction definition in the under-overlap configuration. Letting $C_1 = C_2 = C$, the two coil array element 2010 and 2020 create two local modes and their frequencies are:

$$\omega^2 = \frac{1}{C(L \pm M)} \quad \text{Eq. 29}$$

Putting $$C = \frac{1}{\omega_0^2(L+M)}$$

into Eq. 27 and Eq. 28, then the following results:

$$I_1 = \frac{j\omega_0 B_1 A_1 R + (A_1 - A_2)B_1 M \omega_0^2}{R(R - 2jM\omega_0)} \quad \text{Eq. 30}$$

$$I_2 = -\frac{\omega_0 B_1 A_2 R + j(A_1 - A_2)B_1 M \omega_0^2}{R(jR + 2M\omega_0)} \quad \text{Eq. 31}$$

In this example, assuming $M\omega_0 \gg R$ and A1 and A2 are different, all R terms may be eliminated when R is added or subtracted to any $M\omega_0$ term, thus Eq. 30 and Eq. 31 can be simplified as:

$$I_1 = j\frac{(A_1 - A_2)B_1\omega_0}{2R} \quad \text{Eq. 32}$$

$$I_2 = -\frac{j(A_1 - A_2)B_1\omega_0}{2R} \quad \text{Eq. 33}$$

In this example, single-layer MRI RF coil array elements 2010 and 2020 have the same magnitudes but opposite phases. Since single-layer MRI RF coil array element 2030's area is same as that of single-layer MRI RF coil array element 2020, and since single-layer MRI RF coil array element 2040 has an area the same as that of single-layer MRI RF coil array element 2010, then the induced current of single-layer MRI RF coil array element 2040 will, in this example, be same as that of single-layer MRI RF coil array element 2010. Similarly, the induced current in single-layer MRI RF coil array element 2030 will be same as that of single-layer MRI RF coil array element 2020. This is the same current magnitude and phase configuration as defined in the low heat mode previously.

Embodiments described herein may be configured as a single-layer MRI RF coil array. One embodiment includes a single-layer MRI RF coil array configured to operate in a Tx mode or in an Rx mode during an iMRI procedure. In this embodiment, the coil array includes a plurality of single-layer MRI RF coil array elements (e.g., single-layer MRI RF coil array elements 600, 800, 900, 1000, 1100, 1200, or 1500). A single-layer MRI RF coil array element includes, in this embodiment, an LC coil, a matching and Tx/Rx switch circuit operably connected to the LC coil, a preamplifier operably connected to the matching and Tx/Rx circuit, and a magnitude/phase control component operably connected to the LC coil. In one embodiment, the matching and Tx/Rx switch circuit is a capacitive matching and Tx/Rx switch circuit, while in another embodiment, the matching and Tx/Rx switch circuit is an inductive matching and Tx/Rx switch circuit.

The LC coil includes at least one inductor and at least one capacitor. The at least one inductor and the at least one capacitor resonate at a first frequency.

The matching and Tx/Rx switch circuit, when operating in Tx mode, electrically isolates the LC coil from the preamplifier upon the LC coil resonating with a primary coil. The matching and Tx/Rx switch circuit, when operating in Rx mode, electrically connects the LC coil with the preamplifier. The primary coil has a working frequency.

The LC coil, upon resonating with the primary coil, generates a local amplified Tx field based on an induced current in the LC coil. The induced current is generated by inductive coupling between the LC coil and the primary coil.

A magnitude of the induced current or a phase of the induced current is independently adjustable. The magnitude of the induced current or the phase of the induced current is configured to be varied over a range of magnitudes or phases respectively.

The magnitude/phase control component is configured to adjust the magnitude of the induced current or the phase of the induced current. In one embodiment, the magnitude/phase control component is configured to, upon the single-layer MRI RF coil array element operating in Tx mode, adjust the magnitude of the induced current or the phase of the induced current by shifting the first frequency of the LC coil relative to the working frequency of the primary coil.

In another embodiment, the magnitude/phase control component is configured to, upon the single-layer MRI RF coil array element operating in Tx mode, adjust the magnitude of the induced current or the phase of the induced current by adding coil loss to the LC coil. In this embodiment, the magnitude/phase control component includes a resistor and a PIN diode connected in parallel with the at least one capacitor. The single-layer MRI RF coil array element operates in Tx mode upon the injection of a DC bias into the PIN diode. The DC bias forward biases the PIN diode.

In another embodiment, the magnitude/phase control component is configured to, upon the single-layer MRI RF coil array element operating in Tx mode, adjust the magnitude of the induced current or the phase of the induced current by decreasing the induced current. In this embodiment, the magnitude/phase control component is configured to operate as a parallel resonant circuit when the single-layer MRI RF coil array element operates in Tx mode. In this embodiment, the magnitude/phase control component includes an inductor and a PIN diode connected in parallel with a first member of the at least one capacitor. The first member of the at least one capacitor has a higher capacitance than a second, different member of the at least one capacitor, where the single-layer MRI RF coil array element operates in Tx mode upon the injection of a DC bias into the PIN diode, where the DC bias forward biases the PIN diode. For example, the first member of the at least one capacitor may be a capacitor with a large capacitance value. For example, in one embodiment, 1000 pF is considered a large capacitance value at 63.78 MHz. The impedance of such a capacitor is $-j2.5$ Ohm at 63.78 MHz. 6.24 nH is $+j2.5$ Ohm at 63.78 MHz. 6.24 nH is considered, in this example, as a low inductance value. Thus the Q of the MRI RF coil array element can be low. If the Q is 10 at 63.78 MHz, then the LC resonant circuit will provide approximately 2.5/10*10^2=25 Ohm impedance. Providing this level of impedance facilitates decreasing the magnitude of the induced current significantly. While a 1000 pF capacitor is referred to in this example, other values may be employed.

Figure 21:
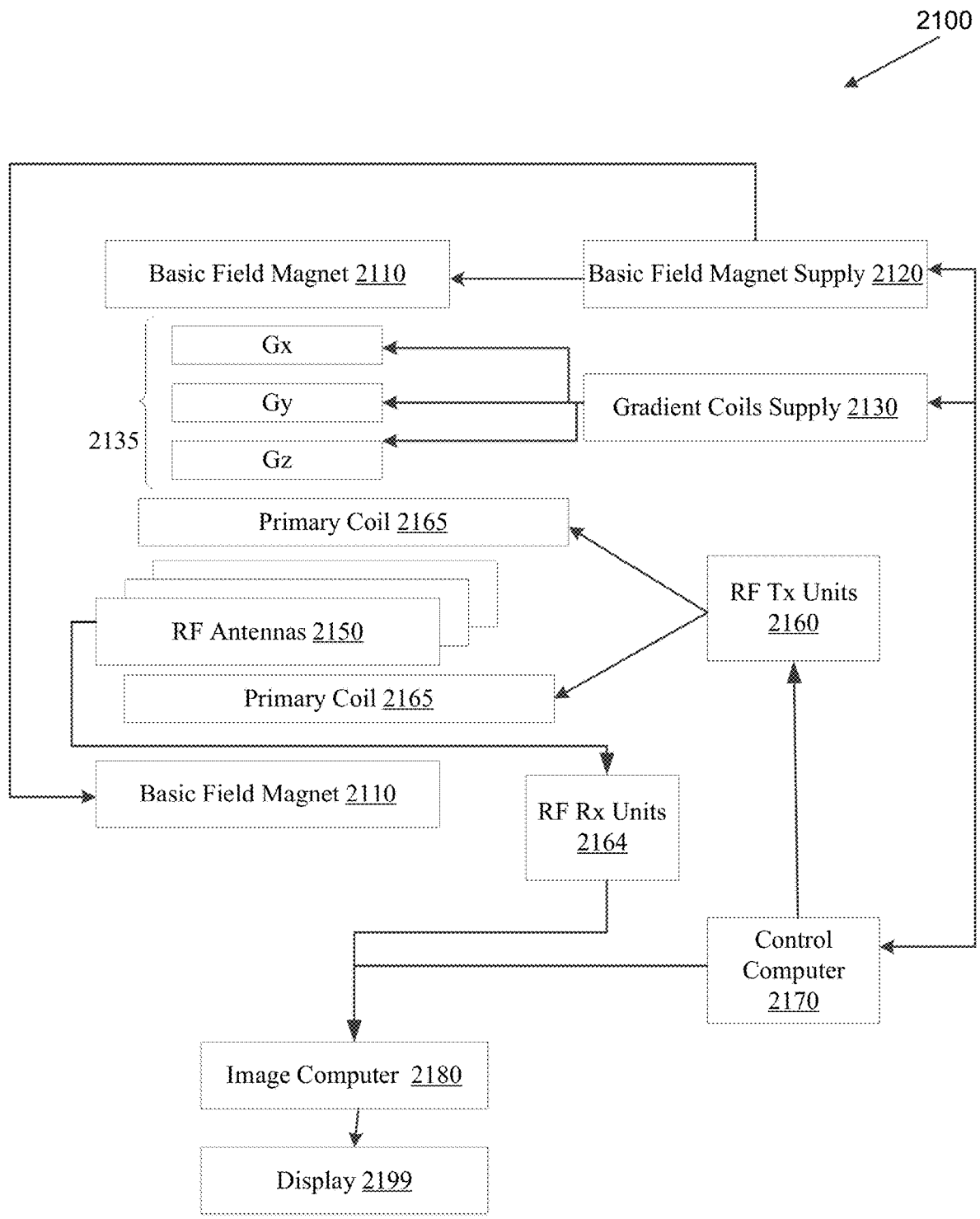
FIG. 21 illustrates an example MRI apparatus.

FIG. 21 illustrates an example MRI apparatus 2100 configured with a set of example single-layer MRI RF coils. MRI apparatus 2100 may be, for example, an iMRI apparatus, or may be operably connected with an iMRI apparatus or iMRI system. The apparatus 2100 includes a basic field magnet(s) 2110 and a basic field magnet supply 2120. Ideally, the basic field magnets 2110 would produce a uniform B0 field. However, in practice, the B0 field may not be uniform, and may vary over an object being imaged by the MRI apparatus 2100. MRI apparatus 2100 may include gradient coils 2135 configured to emit gradient magnetic fields like $G_x$, $G_y$, and $G_z$. The gradient coils 2135 may be controlled, at least in part, by a gradient coils supply 2130. In some examples, the timing, strength, and orientation of the gradient magnetic fields may be controlled, and thus selectively adapted during an MRI procedure.

MRI apparatus 2100 may include a primary coil 2165 configured to generate RF pulses. The primary coil 2165 may be a whole body coil. The primary coil 2165 may be, for example, a birdcage coil. The primary coil 2165 may be controlled, at least in part, by an RF transmission unit 2160. RF transmission unit 2160 may provide a signal to primary coil 2165.

MRI apparatus 2100 may include a set of RF antennas 2150 that are configured to inductively couple with primary coil 2165 and generate RF pulses and to receive resulting magnetic resonance signals from an object to which the RF pulses are directed. In one embodiment, a member of the set of RF antennas 2150 may be fabricated from flexible coaxial cable. The set of RF antennas 2150 may be connected with an RF receive unit 2164.

The gradient coils supply 2130 and the RF transmission units 2160 may be controlled, at least in part, by a control computer 2170. The magnetic resonance signals received from the set of RF antennas 2150 can be employed to generate an image, and thus may be subject to a transformation process like a two dimensional fast Fourier transform (FFT) that generates pixilated image data. The transformation can be performed by an image computer 2180 or other similar processing device. The image data may then be shown on a display 2199. RF Rx Units 2164 may be connected with control computer 2170 or image computer 2180. While FIG. 12 illustrates an example MRI apparatus 2100 that includes various components connected in various ways, it is to be appreciated that other MRI apparatus may include other components connected in other ways.

In one example, MRI apparatus 2100 may include control computer 2170. In one example, a member of the set of RF antennas 2150 may be individually controllable by the control computer 2170. A member of the set of RF antennas 2150 may be an example MRI RF coil element, or an example single-layer MRI RF coil array. For example, MRI RF coil elements 600, 800, 900, 1000, 1100, 1200, or 1500 may be implemented as part of RF antennas 2150 illustrated in FIG. 21. In another embodiment, RF antennas 2150 may include single-layer MRI RF array 2000. In another embodiment, the set of RF antennas 2150 may include other, different combinations of example embodiments of MRI RF coil elements or example embodiments of single-layer MRF RF coil arrays. The magnitude and phase of an induced current in members of RF antennas 2150, including individual coil array elements, may be independently adjustable according to embodiments described herein. Independently adjusting the magnitude and phase of an induced current in members of RF antennas 2150 faciliates adjusting the value of a Tx field generated by RF antennas 2150, and facilitates controlling the heating mode of an iMRI guidewire that may be subjected to the Tx field.

An MRI apparatus may include, among other components, a controller and an RF coil operably connected to the controller. The controller may provide the RF coil with a current, a voltage, or a control signal. The coil may be a whole body coil. The coil may inductively couple with an example MRI RF coil element or single-layer MRI coil array, as described herein, including MRI RF coil element 600, 700, 800, 900, 1000, 1100, 1200, or 1500, or single-layer MRI coil array 2000.

Figure 22:
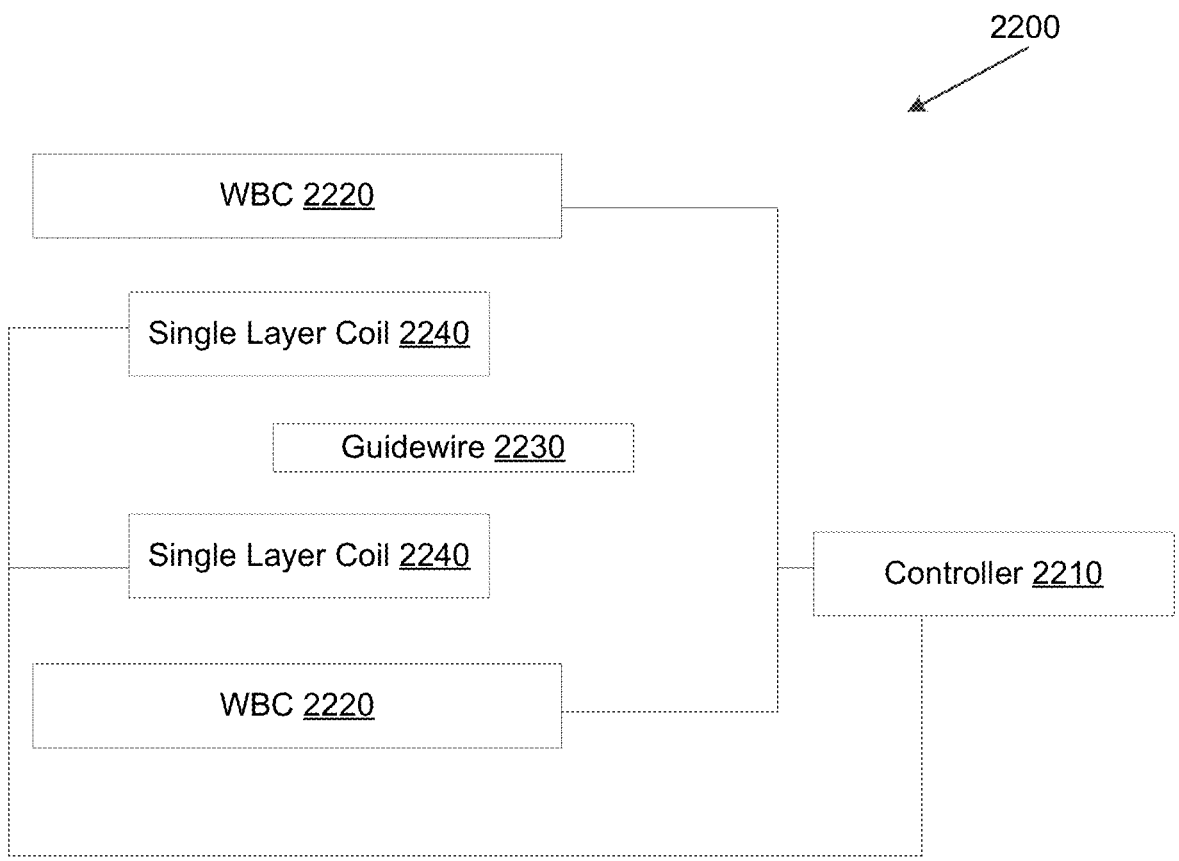
FIG. 22 illustrates an example iMRI apparatus.

FIG. 22 illustrates an interventional magnetic resonance imaging (iMRI) apparatus 2200. In one embodiment, iMRI apparatus may be implemented as part of MRI apparatus, including MRI apparatus 2100, or may be operably connected to an MRI apparatus, including MRI apparatus 2100. iMRI apparatus 2200 includes a controller 2210, a whole body coil (WBC) 2220, an intravascular guidewire 2230, and a single-layer MRI radio frequency (RF) coil 2240 operably connected to the controller 2210. Controller 2210 provides the single-layer MRI RF coil 2240 with a current, a voltage, or a control signal. Controller 2210 may provide a DC bias to single-layer MRI RF coil 2240.

Single-layer MRI RF coil 2240 includes a plurality of transmit (Tx)/receive (Rx) loops, where a member of the plurality of Tx/Rx loops includes a PIN diode, and an induced current magnitude/phase control component. Single-layer MRI RF coil 2240 is configured to operate in an Rx mode and in a Tx mode. A member of the plurality of Rx loops may be, for example, single-layer MRI RF coil array element 1500, or other embodiment described herein. Single-layer MRI RF coil 2240 may be an array of single-layer MRI RF coil array elements, including, for example, single-layer MRI RF coil array 2000 or other embodiment as described herein.

Single-layer MRI RF coil 2240 operates in the Tx mode upon the injection of a DC bias into the PIN diode. The DC bias forward biases the PIN diode. Single-layer MRI RF coil 2240 inductively couples with the WBC 2220 when operating in Tx mode. Single-layer MRI RF coil 2240, upon resonating with the WBC 2220 in Tx mode, induces a local amplified Tx field. The local amplified Tx field is based, at least in part, on an induced current in a member of the plurality of Rx loops, the induced current generated by inductive coupling with the WBC 2220. The uniformity of the local amplified Tx field is varied by adjusting the magnitude of the induced current or the phase of the induced current in a member of the plurality of Tx/Rx loops.

The induced current magnitude/phase control component controls a difference between a working frequency of the WBC 2220 and a resonant frequency of a member of the plurality of Tx/Rx loops, a coil loss resistance of a member of the plurality of Tx/Rx loops, or a blocking impedance of an LC circuit connected in parallel with the member of the plurality of Tx/Rx loops.

The magnitude of the induced current or a phase of the induced current in a member of the plurality of Tx/Rx loops is independently adjustable based, at least in part, on at least one of the difference, the coil loss resistance, or the blocking impedance. The magnitude of the induced current or the phase of the induced current adjusts the uniformity of the local amplified Tx field, and thus controls a heating mode of the guidewire 2230. For example, at a first point in time during an iMRI procedure, the guidewire 2230 may experience a first level of heating while in a first location of the Tx field generated by single-layer MRI RF coil 2240, where the Tx field in the first location is dominated by a first member of the plurality of Tx/Rx loops. Controller 2210 may control the magnitude or phase of a member of the plurality of Tx/Rx loops such that the Tx field is altered, thus changing the level of RF heating induced in the guidewire. At a second, different point in time of the iMRI procedure, the guidewire 2230 may experience RF heating induced by a different location of the Tx field dominated by a second, different member of the plurality of Rx loops. Controller

2210 may then control the magnitude or phase of a second, different member of the plurality of Tx/Rx loops such that the Tx field is altered, thus changing the level of RF heating induced in the guidewire at the second point in time. While two members of the plurality of Tx/Rx loops are described here, embodiments may include more than two Tx/Rx loops, and controller 2210 may control more than two Tx/Rx loops. In one embodiment, guidewire 2230 may be, for example, a catheter or other surgical device subjectable to RF heating during an interventional magnetic resonance procedure.

Figure 23:
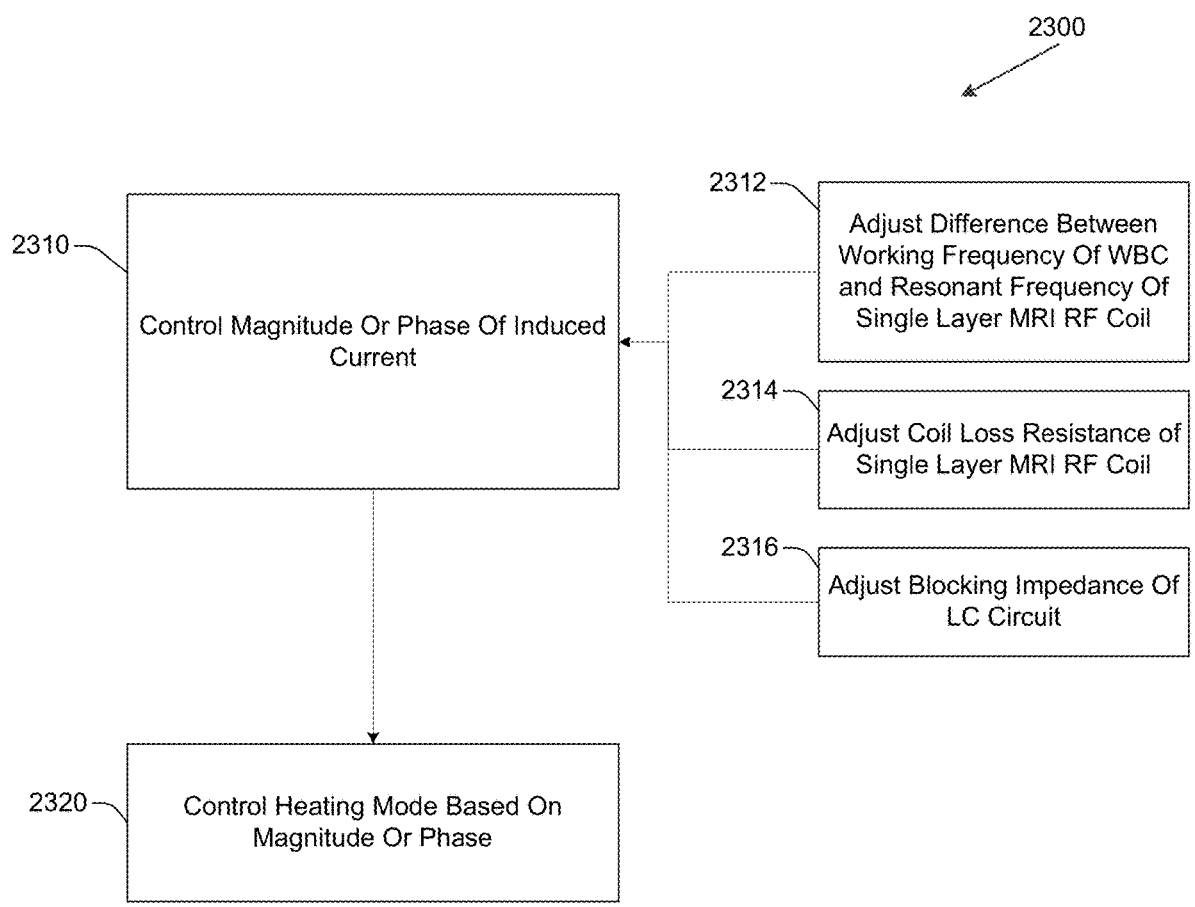
FIG. 23 illustrates an example method for controlling a heating mode of an iMRI guidewire.

FIG. 23 illustrates an example method 2300 for controlling a heating mode of an iMRI guidewire during an iMRI procedure. Method 2300 includes, at 2310 controlling, during an iMRI procedure, a magnitude of an induced current in a single-layer MRI radio frequency (RF) coil used in the iMRI procedure, or a phase of the induced current. Method 2300 may include, at 2312, controlling the magnitude or phase of the induced current by adjusting a difference between a working frequency of a whole body coil (WBC) used in the iMRI procedure and a resonant frequency of the single layer MRI RF coil. Method 2300 may also include, at 2314, controlling the magnitude or phase by adjusting a coil loss resistance of the single layer MRI RF coil. Method 2300 may also include, at 2316, controlling the magnitude or phase by adjusting a blocking impedance of an LC circuit connected in parallel with the single-layer MRI RF coil. In another embodiment, method 2300 controls the heating mode of a catheter, or other device subject to RF heating during an iMRI procedure.

Method 2300 further includes, at 2320, controlling a heating mode of the guidewire based, at least in part on the magnitude or phase of the induced current. Controlling the magnitude or phase of the induced current varies the uniformity of a Tx field generated by the single-layer MRI RF coil. Varying the uniformity of the Tx field changes the heating mode experienced by the guidewire. A heating mode may be a low-heat mode, or other mode.

Circuits, apparatus, elements, MRI RF coils, arrays, and other embodiments described herein are described with reference to the drawings in which like reference numerals are used to refer to like elements throughout, and where the illustrated structures are not necessarily drawn to scale. Embodiments are to cover all modifications, equivalents, and alternatives falling within the scope of the invention. In the figures, the thicknesses of lines, layers and/or regions may be exaggerated for clarity. Nothing in this detailed description (or drawings included herewith) is admitted as prior art.

Like numbers refer to like or similar elements throughout the description of the figures. When an element is referred to as being "connected" to another element, it can be directly connected to the other element or intervening elements may be present. In contrast, when an element is referred to as being "directly connected" to another element, there are no intervening elements present. Other words used to describe the relationship between elements should be interpreted in a like fashion (e.g., "between" versus "directly between," "adjacent" versus "directly adjacent," etc.).

In the above description some components may be displayed in multiple figures carrying the same reference signs, but may not be described multiple times in detail. A detailed description of a component may then apply to that component for all its occurrences.

The following includes definitions of selected terms employed herein. The definitions include various examples or forms of components that fall within the scope of a term and that may be used for implementation. The examples are not intended to be limiting. Both singular and plural forms of terms may be within the definitions.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Circuit", as used herein, includes but is not limited to hardware, firmware, or combinations of each to perform a function(s) or an action(s), or to cause a function or action from another circuit, logic, method, or system. Circuit may include a software controlled microprocessor, a discrete logic (e.g., ASIC), an analog circuit, a digital circuit, a programmed logic device, a memory device containing instructions, and other physical devices. A circuit may include one or more gates, combinations of gates, or other circuit components. Where multiple logical circuits are described, it may be possible to incorporate the multiple logical circuits into one physical circuit. Similarly, where a single logical circuit is described, it may be possible to distribute that single logical logic between multiple physical circuits.

To the extent that the term "includes" or "including" is employed in the detailed description or the claims, it is intended to be inclusive in a manner similar to the term "comprising" as that term is interpreted when employed as a transitional word in a claim.

To the extent that the term "or" is employed in the detailed description or claims (e.g., A or B) it is intended to mean "A or B or both". The term "and/or" is used in the same manner, meaning "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

To the extent that the phrase "one or more of, A, B, and C" is employed herein, (e.g., a data store configured to store one or more of, A, B, and C) it is intended to convey the set of possibilities A, B, C, AB, AC, BC, and/or ABC (e.g., the data store may store only A, only B, only C, A&B, A&C, B&C, and/or A&B&C). It is not intended to require one of A, one of B, and one of C. When the applicants intend to indicate "at least one of A, at least one of B, and at least one of C", then the phrasing "at least one of A, at least one of B, and at least one of C" will be employed.

Although the subject matter has been described in language specific to structural features or methodological acts, it is to be understood that the subject matter defined in the appended claims is not necessarily limited to the specific features or acts described above. Rather, the specific features and acts described above are disclosed as example forms of implementing the claims.

What is claimed is:

1. A single-layer magnetic resonance imaging (MRI) radio frequency (RF) coil array element configured to operate in a transmit (Tx) mode and a receive (Rx) mode during an interventional MRI (iMR) procedure, the single-layer MRI RF coil array element comprising:
   an LC coil;
   a matching and Tx/Rx switch circuit operably connected to the LC coil;

a preamplifier operably connected to the matching and Tx/Rx circuit; and a magnitude/phase control component operably connected to the LC coil;

where the LC coil includes at least one inductor and at least one capacitor, where the at least one inductor and the at least one capacitor resonate at a first frequency;

where the matching and Tx/Rx switch circuit, when operating in Tx mode, electrically isolates the LC coil from the preamplifier upon the LC coil resonating with a primary coil, where the primary coil has a working frequency;

where the LC coil, upon resonating with the primary coil, generates a local amplified Tx field based on an induced current in the LC coil, the induced current generated by inductive coupling between the LC coil and the primary coil;

where a magnitude of the induced current or a phase of the induced current is independently adjustable;

where the magnitude of the induced current or the phase of the induced current is configured to be varied over a range of magnitudes or phases respectively;

where the matching and Tx/Rx switch circuit, when operating in Rx mode, electrically connects the LC coil with the preamplifier; and where the magnitude/phase control component is configured to adjust the magnitude of the induced current or the phase of the induced current at the LC coil by adjusting impedance of the LC coil while the LC coil is wirelessly electrically coupled to a transmitter through the primary coil.

2. A single-layer magnetic resonance imaging (MRI) radio frequency (RF) coil array configured to operate in a transmit (Tx) mode or in a receive (Rx) mode during an interventional MRI (iMRI) procedure, the single-layer MRI RF coil array comprising:

a plurality of single-layer MRI RF coil array elements, where a single-layer MRI RF coil array element of the plurality of single-layer MRI RF coil array elements comprises:

an LC coil;

a matching and Tx/Rx switch circuit operably connected to the LC coil, where the matching and Tx/Rx switch circuit is a capacitive matching and Tx/Rx switch circuit or an inductive matching and Tx/Rx switch circuit;

a preamplifier operably connected to the matching and Tx/Rx circuit; and a magnitude/phase control component operably connected to the LC coil;

where the LC coil includes at least one inductor and at least one capacitor, where the at least one inductor and the at least one capacitor resonate at a first frequency, and where the at least one capacitor comprises a first capacitor;

where the matching and Tx/Rx switch circuit, when operating in Tx mode, electrically isolates the LC coil from the preamplifier upon the LC coil resonating with a primary coil, where the primary coil has a working frequency;

where the LC coil, upon resonating with the primary coil, generates a local amplified Tx field based on an induced current in the LC coil, the induced current generated by inductive coupling between the LC coil and the primary coil;

where a magnitude of the induced current or a phase of the induced current is independently adjustable;

where the magnitude of the induced current or the phase of the induced current is configured to be varied over a range of magnitudes or phases respectively;

where the matching and Tx/Rx switch circuit, when operating in Rx mode, electrically connects the LC coil with the preamplifier; and where the magnitude/phase control component is configured to adjust the magnitude of the induced current or the phase of the induced current, where adjusting the magnitude of the induced current or the phase of the induced current adjusts a heating mode of an iMRI guidewire employed during the iMRI procedure, where the magnitude/phase control component comprises a first switch and a first resistive or reactive component bordering the LC coil, where the first switch is configured to electrically couple the first resistive or reactive component in parallel with the first capacitor while in an ON state and to remove the first resistive or reactive component from in parallel with the first capacitor while in an OFF state, and where the magnitude/phase control component is configured to adjust the magnitude or phase while in Tx mode by changing the first switch between the ON and OFF states.

3. An interventional magnetic resonance imaging (iMRI) apparatus, comprising:

a controller;

a whole body coil (WBC);

an intravascular guidewire; and a single-layer MRI radio frequency (RF) coil operably connected to the controller;

where the controller provides the single-layer MRI RF coil with a current, a voltage, or a control signal;

where the single-layer MRI RF coil includes a plurality of receive (Rx) loops, where a member of the plurality of Rx loops comprises a PIN diode, a first capacitor, a second capacitor, and an induced current magnitude/phase control component, where the single-layer MRI RF coil is configured to operate in a Rx mode and in a transmit (Tx) mode, where the single-layer MRI RF coil operates in the Tx mode upon the injection of a DC bias into the PIN diode, where the DC bias forward biases the PIN diode, where the single-layer MRI RF coil inductively couples with the WBC when operating in the Tx mode, where the single-layer MRI RF coil, upon resonating with the WBC in Tx mode, induces a uniform local amplified Tx field, where the uniform local amplified Tx field is based, at least in part, on an induced current in the single-layer MRI RF coil, where the induced current magnitude/phase control component controls a difference between a working frequency of the WBC and a resonant frequency of the single-layer MRI RF coil, a coil loss resistance of the single-layer MRI RF coil, or a blocking impedance of an LC circuit connected in parallel with the single-layer MRI RF coil, where a magnitude of the induced current or a phase of the induced current is independently adjustable based, at least in part, on at least one of the difference, the coil loss resistance, or the blocking impedance; and where the magnitude of the induced current or the phase of the induced current controls a heating mode of the intravascular guidewire, where the induced current magnitude/phase control component comprises a first circuit leg and a second circuit leg, where the first and second circuit legs each comprises a diode switch and an electronic component electrically coupled in series with the diode switch, where the first circuit leg is electrically coupled in parallel with the first capacitor, where the second circuit leg is electrically coupled in parallel with the first or second capacitor, where the electronic component is a resistor, a capacitor, or an inductor, and where the controller is configured to control ON/OFF states of the diode switch of the first circuit leg and the diode switch of the second circuit leg to change the phase and/or the magnitude of the induced current in the Tx mode.

4. The single-layer MRI RF coil array element of claim 1, where the magnitude/phase control component is configured to, upon the single-layer MRI RF coil array element operating in Tx mode, adjust the magnitude of the induced current or the phase of the induced current by shifting the first frequency of the LC coil relative to the working frequency of the primary coil.

5. The single-layer MRI RF coil array element of claim 1, where the magnitude/phase control component is configured to, upon the single-layer MRI RF coil array element operating in Tx mode, adjust the magnitude of the induced current or the phase of the induced current by decreasing the induced current.

6. The single-layer MRI RF coil array element of claim 5, where the magnitude/phase control component is configured to decrease the induced current by operating as a parallel resonant circuit when in Tx mode.

7. The single-layer MRI RF coil array element of claim 6, where the magnitude/phase control component comprises an inductor and a PIN diode connected in parallel with a first member of the at least one capacitor, where the first member of the at least one capacitor has a higher capacitance than a second, different member of the at least one capacitor, where the single-layer MRI RF coil array element operates in Tx mode upon the injection of a DC bias into the PIN diode, where the DC bias forward biases the PIN diode.

8. The single-layer MRI RF coil array element of claim 1, where the matching and Tx/Rx switch circuit is a capacitive matching and Tx/Rx switch circuit.

9. The single-layer MRI RF coil array element of claim 1, where the matching and Tx/Rx switch circuit is an inductive matching and Tx/Rx switch circuit.

10. The single-layer MRI RF coil array element of claim 1, where the LC coil includes at least one conductor, where the at least one conductor is a flexible co-axial cable.

11. The single-layer MRI RF coil array element of claim 1, further comprising a shunt PIN diode having a first terminal connected to a first input terminal of the preamplifier, and a second terminal connected to a second input terminal of the preamplifier, where, upon application of a forward bias to the shunt PIN diode, the shunt PIN diode provides shunt protection to the preamplifier.

12. The single-layer MRI RF coil array element of claim 1, where the at least one capacitor comprises a first capacitor and a second capacitor, where the magnitude/phase control component comprises a first diode switch, a second diode switch, a first electronic component, and a second electronic component, where the first diode switch and the first electronic component have individual first terminals electrically shorted together and further have individual second terminals electrically shorted respectively to a first terminal of the first capacitor and a second terminal of the first capacitor, where the second diode switch and the second electronic component have individual first terminals electrically shorted together and further have individual second terminals electrically shorted respectively to the first terminal of the first capacitor and the second terminal of the first capacitor, and where each of the first and second electronic components is a resistor, a capacitor, or an inductor.

13. The single-layer MRI RF coil array element of claim 12, where the first diode switch comprises a pair of first PIN diodes, and where the first PIN diodes have individual anodes electrically shorted together and have individual cathodes respectively and electrically shorted to the first terminal of the first electronic component and the first terminal of the first capacitor.

14. The single-layer MRI RF coil array of claim 2, where the magnitude/phase control component is configured to, upon the single-layer MRI RF coil array element operating in Tx mode, adjust the magnitude of the induced current or the phase of the induced current by adding coil loss to the LC coil.

15. The single-layer MRI RF coil array of claim 14, where the first switch and the first resistive or reactive component are respectively a PIN diode and a resistor, where the single-layer MRI RF coil array element operates in Tx mode upon the injection of a DC bias into the PIN diode, where the DC bias forward biases the PIN diode.

16. The single-layer MRI RF coil array of claim 2, where the at least one capacitor further comprises a second capacitor, where the first switch and the first resistive or reactive component are respectively a PIN diode and an inductor, where the first capacitor has a higher capacitance than the second capacitor, where the single-layer MRI RF coil array element operates in Tx mode upon the injection of a DC bias into the PIN diode, where the DC bias forward biases the PIN diode.

17. The single-layer MRI RF coil array of claim 16, where the magnitude/phase control component introduces a blocking impedance of less than one-hundred Ohms to the LC coil when the single-layer MRI RF coil array element operates in Tx mode.

18. The single-layer MRI RF coil array of claim 2, where the at least one capacitor comprises a second capacitor, where the magnitude/phase control component further comprises a second switch and a second resistive or reactive component, where the second switch is configured to electrically couple the second resistive or reactive component in parallel with the second capacitor while in an ON state and to remove the second resistive or reactive component from in parallel with the second capacitor while in an OFF state, and where the magnitude/phase control component is configured to adjust the magnitude or the phase while in Tx mode by further changing the second switch between the ON and OFF states.

19. A non-transitory computer-readable storage device storing computer executable instructions that when executed by a computer control the computer to perform a method for controlling a heating mode of an interventional magnetic resonance imaging (iMRI) guidewire, the method comprising:
  controlling, during an iMRI procedure, a magnitude of an induced current in a single-layer MRI radio frequency (RF) coil used in the iMRI procedure, or a phase of the induced current, by adjusting at least one of:
    a difference between a working frequency of a whole body coil (WBC) used in the iMRI procedure and a resonant frequency of the single-layer MRI RF coil,
    a coil loss resistance of the single-layer MRI RF coil, or a blocking impedance of an LC circuit connected in parallel with the single-layer MRI RF coil; and controlling a heating mode of the iMRI guidewire based, at least in part on the magnitude or the phase;

where the single-layer MRI radio frequency (RF) coil comprises an inductor-capacitor (LC) coil, wherein the LC coil comprises a first capacitor, where the controlling of the magnitude or the phase and the controlling of the heating mode comprises adding a first electronic component in parallel with the first capacitor, or removing the first electronic component from in parallel with the first capacitor, at the LC coil, and where the first electronic component is a resistor, a capacitor, or an inductor.

20. The iMRI apparatus of claim 3, where the first and second circuit legs each consists of the diode switch and the electronic component electrically coupled in series with the diode switch, and where the controller controls the diode switch of the first circuit leg and the diode switch of the second circuit leg so only one diode switch is ON at any given time in the Tx mode.

21. The non-transitory computer-readable storage device of claim 19, where the LC coil further comprises a second capacitor, where the controlling of the magnitude or the phase and the controlling of the heating mode comprises adding a second electronic component in parallel with the first or second capacitor, or removing the second electronic component from in parallel with the first or second capacitor, at the LC coil, and where the second electronic component is independent of the first electronic component and is a resistor, a capacitor, or an inductor.

22. The non-transitory computer-readable storage device of claim 21, where the adding and the removing of the first electronic component are performed by respectively forward biasing and reverse biasing a first PIN diode electrically coupled directly to the first electronic component, and where the adding and the removing of the second electronic component are performed by respectively forward biasing and reverse biasing a second PIN diode electrically coupled directly to the second electronic component.

* * * * *